US008241646B2

(12) United States Patent (10) Patent No.: US 8,241,646 B2
Goetsch et al. (45) Date of Patent: Aug. 14, 2012

(54) METHOD FOR GENERATING ACTIVE ANTIBODIES AGAINST A RESISTANCE ANTIGEN, ANTIBODIES OBTAINED BY SAID METHOD AND THEIR USES

(75) Inventors: Liliane Goetsch, Ayze (FR); Alexandra Jouhanneaud, Bonneville (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 137 days.

(21) Appl. No.: 12/442,918

(22) PCT Filed: Sep. 27, 2007

(86) PCT No.: PCT/EP2007/060243
§ 371 (c)(1),
(2), (4) Date: May 14, 2009

(87) PCT Pub. No.: WO2008/046724
PCT Pub. Date: Apr. 24, 2008

(65) Prior Publication Data
US 2010/0146650 A1 Jun. 10, 2010

(30) Foreign Application Priority Data
Sep. 28, 2006 (FR) .................................... 06 08514

(51) Int. Cl.
*A61K 39/395* (2006.01)
*A61K 35/12* (2006.01)
(52) U.S. Cl. .................................... 424/277.1; 424/573
(58) Field of Classification Search ........................ None
See application file for complete search history.

(56) References Cited

U.S. PATENT DOCUMENTS
5,503,984 A 4/1996 Chu et al.

FOREIGN PATENT DOCUMENTS
| EP | 0214640 A2 | 3/1987 |
| WO | WO-93/25700 A1 | 12/1993 |
| WO | WO-99/66027 A1 | 12/1999 |
| WO | WO2006077160 * | 7/2006 |

OTHER PUBLICATIONS

Clark (Protein Engineering of Antibody Molecules for Prophylactic and Therapeutic Applications in Man, 1993, pp. 4-5).*
Giavazzi et al ('Heterogeneous Malignant Behaviour and Drug Respsonse Among Human Ovarain Carcainoma Xenografts', In: Heterogeneity of Cancer Cells, D'Incalci et al, Ed.s, 1993, pp. 41-47).*
"Drug Facts and Comparisons", 1999, Kastrup et al, Ed.s, p. 3289).*
Schlom (Monoclonal Antibodies: They're More and Less Than You Think, In: Molefular Foundations of Oncology, S. Broder, Ed., 1991, pp. 95-134.*
Wang et al (BBRC, 1997, vol. 236, pp. 483-488).*
"Drug Facts and Comparisons", 1999, Kastrup et al, Ed.s, pp. 3285-3300).*
Smith et al.; "Comparison of Biosequences", Advances in Applied Mathematics 2, (1981), pp. 482-489.
Kaufman et al.; "Clinical Strategies for Cancer Treatment: The Role of Drugs", Cancer Chemotherapy and Biotherapy, Second Edition, (1996), pp. 1-16.
Lehnert; "Clinical Multidrug Resistance in Cancer: A Multifactorial Problem", European Journal of Cancer vol. 32A, No. 6, (1996), pp. 912-920.
Hooper et al.; "Substractive Immunization using Highly Metastic Human Tumor Cells Identifies SIMA135/CDCP1, a 135kDk Cell Surface Phosphorylated Glycoprotein Antigen", Oncogene, 2003, pp. 1783-1794, XP-002283018.
Williams et al.; "Substractive Immunization Techniques for the Production of Monoclonal Antibodies to Rare Antigens" Research Report, vol. 12, No. 6, Jun. 1992, pp. 842-847, XP-000974106.
Repp et al.; "G-CSF-Stimulated PMN in Immunotherapy of Breast Cancer with a Bispecific Antibody to Fc γRI and to HER-2/neu (MDX-210)", Journal of Hematotherapy 4, (1995), pp. 415-421.
Ridder et al.; "Generation of Rabbit Monoclonal Antibody Fragments from a Combinatorial Phage Display Library and Their Production in the Yeast *Pichia pastoris*", Bio/Technology vol. 13, Mar. 1995, pp. 255-260.
Brooks et al.; "Substractive Immunization Yields Monoclonal Antibodies that Specifically Inhibit Metasis", The Journal of Cell Biology, vol. 122, No. 6, Sep. 1993, pp. 1351-1359.
Kozbor et al.; "A Comparative Analysis of the Phenotypic Characteristics of Available Fusion Partners for the Construction of Human Hybridomas", Hybridoma, vol. 2, No. 1983, pp. 7-16.
Merchant et al.; "An Efficient Route to Human Bispecific IgG", Nature Biotechnology vol. 16, Jul. 1998, pp. 677-681.
Morrison et al.; "Chimeric Human Antibody Molecules: Mouse Antigen-Binding Domains with Human Constant Region Domains", Proc. Natl. Acad. Sci. USA, vol. 81, Nov. 1984, pp. 6851-6855.
Kabat et al.; "Sequences of Proteins of Immunological Interest", 6 Volumns.
Glennie et al.; "Preparation and Performance of Bispecific F(ab'γ)2 Antibody Containing Thioether-Linked Fab'γ Fragments", The Journal of Immunology, vol. 139, No. 7, Oct. 1, 1987, pp. 2367-2375.
Pearson et al.; "Improved Tools for Biological Sequence Comparison", Proc. Natl. Acad. Sci., vol. 85, Apr. 1988, pp. 2444-2448.
Segal et al.; "The Three-Dimensional Structure of a Phosphoryleholine-Binding Mouse Immunoglobulin Fab and the nature of the Antigen Binding Site" Proc. Natl. Acad. Sci. vol. 71, No. 11, Nov. 1974, pp. 4298-4302.

(Continued)

*Primary Examiner* — Karen Canella
(74) *Attorney, Agent, or Firm* — Birch, Stewart, Kolasch & Birch, LLP

(57) ABSTRACT

The present invention relates to the use of a milled homogenate and/or a suspension and/or a cell lysate, stemming from a tumor resistant to at least one anti-tumoral compound in order to immunize and generate in vitro an antibody, or one of its functional fragments, directed against a tumoral antigen specifically expressed at the surface of said resistant tumor and being possibly involved in the resistance of said resistant tumor. More particularly, the present invention is directed to such antibodies obtained by applying the method, such as the antibodies 1A6, 1A9, 2E11, 3C11 and 3G7, as well as to their use for treating cancer.

23 Claims, 10 Drawing Sheets

OTHER PUBLICATIONS

Figure 1:
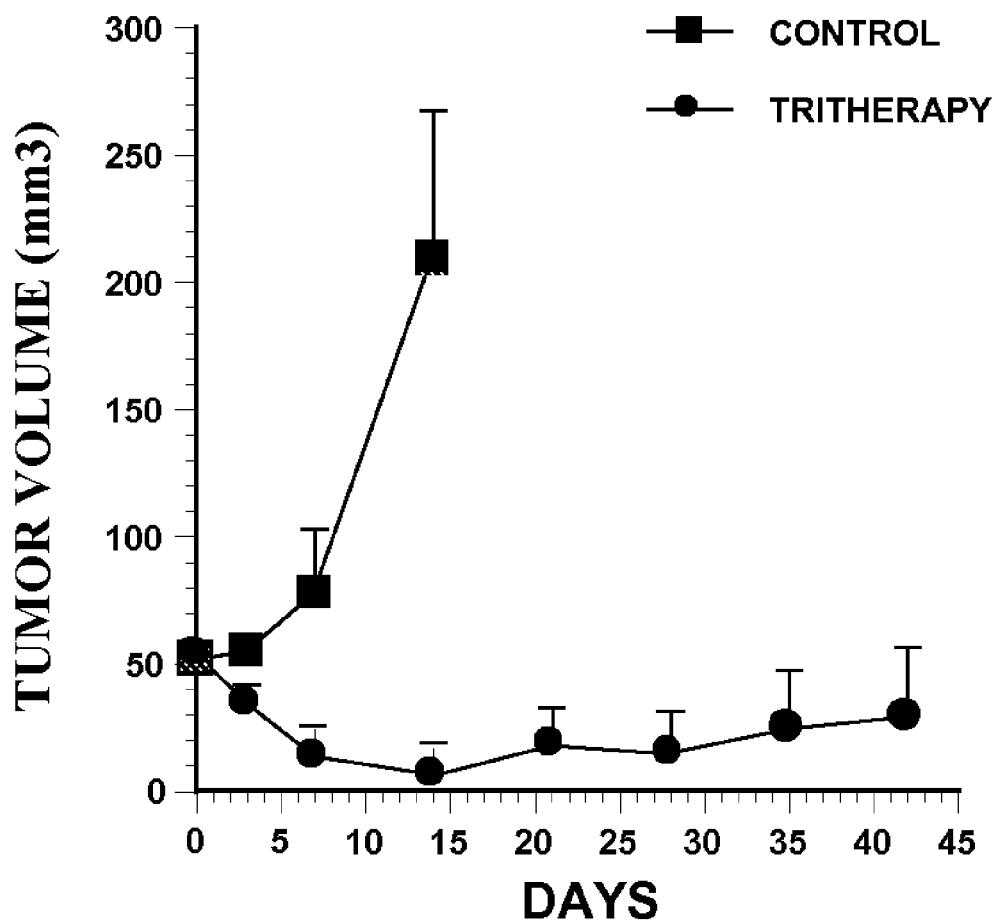

Chothia et al.; "Canonical Structure for the Hypervariable Regions of Immunoglobulins", J. Mol. Biol., vol. 196, (1987) pp. 901-917.

Caton et al.; "Identical D Region Sequences Expressed by Murine Monoclonal Antibodies Specific for a Human Tumor-Associated Antigen", The Journal of Immunology, vol. 144, Nov. 5, Mar. 1, 1990, pp. 1965-1968.

Sharon; "Structural Characterization of Idiotopes by Using Antibody Variants Generated by Site-Directed Mutagenesis", The Journal of Immunology, vol. 144, No. 12, Jun. 15, 1990, pp. 4863-4869.

Staerz et al.; "Hybrid Hybridoma Producing a Bispecific Monoclonal Antibody that can Focus Effector T-Cell Activy", Proc. Natl. Acad. Sci. vol. 83 Mar. 1986, pp. 1453-1457.

Park et al.; "Generation and Characterization of a Novel Tetravalent Bispecific Antibody that Binds to Hepatitis B Virus Surface Antigens", Molecular Immunology, vol. 37, (2000), pp. 1123-1130.

Köhler et al.; "Continuous Cultures of Fused Cells Secreting Antibody of Predefined Specifity", Nature, vol. 256, Aug. 7, 1975, pp. 495-497.

Singer et al.; "Optimal Humanization of 1B4, an Anti-CD18 Murine Monoclonal Antibody, is Achieved by Correct Choice of Human V-Region Framework Sequences", The Journal of Immunology, vol. 150, No. 7, Apr. 1, 1993, pp. 2844-2857.

Needleman et al.; "A General Method Applicable to the Search for Similarities in the Amino Acid Sequence of Two Proteins", J. Mol. Biol. (1979), pp. 443-453.

Tatusova et al.; "BLAST 2 Sequences, a New Tool for Comparing Protein and Nucleotide Sequences", FEMS Microbiology Letters, vol. 174, (1999), pp. 247-250.

Amit et al.; "Three-Dimensional Structure of an Antigen-Antibody Complex at 2.8 Å Resolution", vol. 233, Aug. 15, 1986, pp. 747-753.

Chothia et al.; "Conformations of Immunoglobulin Hypervariable Regions", Nature, vol. 342, Dec. 21-28, 1989, pp. 877-883.

Sharon et al.; "Structural Correlates of High Antibody Affinity: Three Engineered Amino Acid Substitutions can Increase the Affinity of an Anti-$p$-azophenylarsonate antibody 200-fold", Proc. Natl. Acad. Sci. vol. 87, Jun. 1990, pp. 4814-4817.

Kabat et al.; "Identical V Region Amino Acid Sequences and Segments of Sequences in Antibodies of Different Specificities", The Journal of Immunology, vol. 147, No. 5, Sep. 1, 1991, pp. 1709-1719.

Hollinger et al.; "Engineering Antibodies for the Clinic", Cancer and Metastasis Reviews, vol. 18, (1999), pp. 411-419.

Jones et al.; "Replacing the Complementarity-Determining Regions in a Human Antibody with those from a Mouse", Nature, vol. 321, May 29, 1986, pp. 522-525.

Bebbington et al.; "High-Level Expression of a Recombinant Antibody from Myeloma Cells Using a Glutamine Synthetase Gene as an Amplifiable Selectable Marker", Bio/Technology, vol. 10, Feb. 1992, pp. 169-175.

Suresh et al.; "Bispecific Monoclonal Antibodies from Hybrid Hybridomas", Methods in Enzymology, vol. 121, 1986, pp. 210-228.

Verhoeyen et al.; "Engineering of Antibodies", BioEssays, vol. 8, No. 2. Feb./Mar. 1988, pp. 74-78.

* cited by examiner

| Hybridoma | Clone | # NH | Isotype | In vivo model |
|---|---|---|---|---|
| 1A6 D1 | C7 |  | IgM k | MCF7/Colo205 |
|  | D10 | 1 |  | LnCap/HT29 |
| 1A9C12 | E11 | 2 | IgG1 k | HepG2/H69/LnCap |
|  | F1 |  |  |  |
| 2E11B4 | A2 | 3 | IgG1 k | HT29/BxPC3/H69 |
|  | B11 |  |  |  |
| 2E11E1 | A8 | 4 | IgG1 k | HT29/BxPC3/H69 |
|  | B9 |  |  |  |
| 3C11E9 | E8 | 5 | IgM k | Colo205 |
|  | E9 |  |  |  |
| 3G7E11 | A7 | 6 | IgM | DU145 |
|  | B2 |  |  |  |

FIGURE 4

Antibody 1A6

*Heavy chain:*

Nucleotide sequence:
GAGGTCCAGCTGCAACAGTCTGGACCTGAGCTGGTGAAGCCTGGGGCTTCAGTGAAGATATC CTGCAAGACTTCTGGATACACATTCACTGAATACACCTTGCACTGGGTGAAGCAGAGCCATG
<u>                         CDR-1               </u>
GAAAGAGCCTTGAGTGGATTGGAGGTATTGATCCTAACAATGGTGGTACTAGCTATAACCAG
<u>                        CDR-2                                    </u>
AAGTTCAAGGGCAAGGCCACATTGACTGTAGACAAGTCCTCCAGCACAGCCTACATGGAGCT
<u>CDR-2 (cont.)</u>

CCGCAGCCTGACATCTGAGGATTCTGCAGTCTATCTCTGTGCAAGATCGAACAGTTACTACT
<u>                                                CDR-3           </u>
TTGACTACTGGGGCCAAGGCACCACTCTCACAGTCTCCTCA
<u>CDR-3</u>

Protein sequence: (1 letter code)
EVQLQQSGPELVKPGASVKISCKTSGYTFTEYTLHWVKQSHGKSLEWIGGIDPNNGGTSYNQ
                              <u>CDR-1</u>                  <u>CDR-2</u>
KFKGKATLTVDKSSSTAYMELRSLTSEDSAVYLCARSNSYYFDYWGQGTTLTVSS
<u>    </u>                                <u>CDR-3   </u>

*Light chain:*

Nucleotide sequence:
GATATCCAGATGACACAGACTACATCCTCCCTGTCTGCCTCTCTGGGAGACAGCGTCACCAT CAGTTGCAGGGCAAGGCAGGACATTCGCAATTTTTTAAACTGGTATCAGCAGAGACCAGATG
<u>       CDR-1                             </u>
GAACTGTTAAACTCCTGATCTACTACACCTCAAGATTACACTCAGGAGTCCCATCAAGGTTC
<u>                        CDR-2                </u>
AGTGGCAGTGGGTCTGGAACAGATTATTCTCTCACCATTAGCAACCTGGACCAAGAAGATGT TGCCACTTATTTTGCCAACAGGGTAATACGCTTCCATTCACGTTCGGCTCGGGGACAAAGT
<u>                CDR-3                     </u>
TGGAAATAAAA

Protein sequence: (1 letter code)
DIQMTQTTSSLSASLGDSVTISCRARQDIRNFLNWYQQRPDGTVKLLIYYTSRLHSGVPSRF
                       <u>CDR-1      </u>                <u>CDR-2  </u>
SGSGSGTDYSLTISNLDQEDVATYFCQQGNTLPFTFGSGTKLEIK
                          <u>CDR-3    </u>

FIGURE 6

Antibody 1A9

*Heavy chain:*

Nucleotide sequence:

CAGATCCAGTTGGTGCAGTCTGGACCTGAGCTGAAGAAGCCTGGAGAGACAGTCAAGATCTC

CTGCAAGGCTTCTGGGCAGACCTTCACAAACTATGGAATGAACTGGGTGAAGCAGGCTCCAG
<u>                         CDR-1                                </u>

GAAAGGGTTTAAAGTGGATGGGCTGGATAAACACCTACACTGGAGAGCCAACATATGCTGAT
                        <u>                     CDR-2            </u>

GACTTCAAGGGACGGTTTGCCTTCTCTTTGGAAACCTCTGCCAGCACTGCCTATTTGCAGAT

CAACAACCTCAAAAATGAGGACACGGCTACATATTTCTGTGCAAGAGGGGGCTACTATAGGT
                                              <u>          CDR-3</u>

ACGCGGCTTACTGGGGCCAAGGGACTCTGGTCACTGTCTCTGCA

Protein sequence: (1 letter code)
QIQLVQSGPELKKPGETVKISCKASGQTFTNYGMNWVKQAPGKGLKWMGWINTYTGEPTYAD
                             <u>CDR-1</u>                <u>   CDR-2    </u>
DFKGRFAFSLETSASTAYLQINNLKNEDTATYFCARGGYYRYAAYWGQGTLVTVSA
                                      <u>  CDR-3  </u>

*Light chain:*

Nucleotide sequence:
GACATCCAGATGACTCAGTCTCCAGCCTCCCTATCTGCATCTGTGGGAGAAACTGTCACCAT CACATGTCGAGCAAGTGGGAATATTCACAATTATTTAGCATGGTATCAGCAGAAACAGGGAA
       <u>              CDR-1             </u>

AATCTCCTCAGCTCCTGGTCTATAATGCAAAAACCTTAGCAGATGGTGTGCCATCAAGGTTC
                        <u>       CDR-2       </u>

AGTGGCAGTGGATCAGGAACACAATATTCTCTCAAGATCAACAGCCTGCAGCCTGAAGATTT

TGGGTGTTATTTCTGTCAACATTTTTGGACTACTCCGTACACATTCGGAGGGGGGACCAAAC
                <u>           CDR-3          </u>
TGGAACTAATA

Protein sequence: (1 letter code)
DIQMTQSPASLSASVGETVTITCRASGNIHNYLAWYQQKQGKSPQLLVYNAKTLADGVPSRF
                       <u>   CDR-1   </u>                <u> CDR-2 </u>
SGSGSGTQYSLKINSLQPEDFGCYFCQHFWTTPYTFGGGTKLELI
                          <u>  CDR-3  </u>

FIGURE 6(continue)

Antibody 2E11

*Heavy chain:*

Nucleotide sequence:
GAGGTTCAGCTGCAGCAGTCTGGGGCAGAGGTTGTGAAGCCAGGGGCCTCAGTCAAGTTGTC CTGCACAGCTTCTGGCTTCAACATTAAAGACACCTATATGCACTGGGTGAAACAGAGGCCTG
                                    CDR-1
AACAGGGCCTGGAGTGGATTGGAAGGATTGATCCTGCGAATGGAAATACTAAATCTGACCCG
                              CDR-2
AAGTTCCAGGGCAAGGCCATTAAAACAGCAGACACATCCTCCAACACAGCCTACCTTCAGCT CAGTAGCCTGACATCTGAGGACACTGCCGTCTATTACTGTACTAGCGGATATACTAACTACG
                                                         CDR-3
TTTGGTTTACTTACTGGGGCCAAGGGACTCTGGTCACTGTCTCTGCA

Protein sequence: (1 letter code)
EVQLQQSGAEVVKPGASVKLSCTASGFNIKDTYMHWVKQRPEQGLEWIGRIDPANGNTKSDP
                                 CDR-1                   CDR-2
KFQGKAIKTADTSSNTAYLQLSSLTSEDTAVYYCTSGYTNYVWFTYWGQGTLVTVSA
                                          CDR-3

*Light chain:*

Nucleotide sequence:

GACATTGTGATGTCACAGTCTCCATCCTCCCTGGCTGTGGCAGCAGGAGAGAAGGTCACTAT

GAGCTGCAAAGCCAGTCAGAGTCTGCTCAACAGTAGAACCCGAAAGAACTACTTGGCTTGGT
              CDR-1
ACCAGCAGAAACCAGGGCAGTCTCCTAAACTGCTGATCTACTGGGCATCCACTAGGGAATCT
                                                CDR-2
GGGGTCCCTGATCGCTTCACAGGCAGTGGATCTGGGACAGATTTCAGTCTCACCATCAGCAG

TGTGCAGGCTGAAGACCTGGCAGTTTATTACTGCAAGCAATCTTATAATCTGTACACGTTCG
                                         CDR-3
GAGGGGGGACCAAGCTGGAAATAAAA

Protein sequence: (1 letter code)
DIVMSQSPSSLAVAAGEKVTMSCKASQSLLNSRTRKNYLAWYQQKPGQSPKLLIYWASTRES
                              CDR-1                              CDR-2
GVPDRFTGSGSGTDFSLTISSVQAEDLAVYYCKQSYNLYTFGGGTKLEIK
                                   CDR-3

FIGURE 6(continue)

Antibody 3C11

*Heavy chain:*

Nucleotide sequence:
CAGGTGCAGCTGAAGGAGTCAGGACCTGGCCTGGTGGCGCCCTCACAGAGCCTGTCCATCAC TTGCACTGTCTCTGGGTTTTCATTATCCAGCTATGGTGTACACTGGGTTCGCCAGCCTCCAG
                            CDR-1

GAAAGGGTCTGGAGTGGCTGGGAGTAATATGGGTTGGTGGAACCACAAATTTTAAATCGGCT
                                       CDR-2

CTCATGTCCAGACTGAGCATCAGCAAAGACAACTCCAAGAGCCAAGTTTTCTTAAAAATGAA

CAGTCTGCAAACTGATGACACAGCCATGTACTACTGTGCCAGAGAGAGACCCTATGGTAACC
                                                  CDR-3

CTTTGGTTGACTGGGGCCAAGGGACTCTGGTCACTGTCTCTGCA

Protein sequence: (1 letter code)
QVQLKESGPGLVAPSQSLSITCTVSGFSLSSYGVHWVRQPPGKGLEWLGVIWVGGTTNFKSA
                             CDR-1                                CDR-2
LMSRLSISKDNSKSQVFLKMNSLQTDDTAMYYCARERPYGNPLVDWGQGTLVTVSA
                                                 CDR-3

*Light chain:*

Nucleotide sequence:
GACATTGTGATGACCCAGTCTCACAAATTCATGTCCACATCAGTAGGAGACAGGGTCAGCAT CACCTGCAAGGCCAGTCAGGATGTGAGTACTGCTGTCGCCTGGTATCAACAGAAACCAGGAC
                         CDR-1

AATCTCCTAAACTACTGATTTACTCGGCATCCTACCGTTACACTGGAGTCCCTGATCGCTTC
                                          CDR-2

ACTGGCAGTGGATCTGGGACGGATTTCACTTTCACCATCAGCAGTGTGCAGGCTGAAGACCT

GGCAGTTTATTACTGTCAGCAACATTATAGTAATCCTCGGACGTTCGGTGGAGGCACCAAGC
                                      CDR-3

TGGAAATCAAA

Protein sequence: (1 letter code)
DIVMTQSHKFMSTSVGDRVSITCKASQDVSTAVAWYQQKPGQSPKLLIYSASYRYTGVPDRF
                       CDR-1                                    CDR-2
TGSGSGTDFTFTISSVQAEDLAVYYCQQHYSNPRTFGGGTKLEIK
                           CDR-3

FIGURE 6(continue)

Antibody 3G7

*Heavy chain:*
Nucleotide sequence:
CAGGTCCAGTTGCAGCAGTCTGGACCCGAGCTGGTAAGGCCTGGGACTTCAGTGAAGATA TCCTGCAAGGCCTCTGGCTACACCTTCACTAACTACTGGCTAGGTTGGGTAAAGCAGAGGCC
                                                      CDR-1

TGGACATGGACTTGAGTGGATTGGAGATATTTTCCCTGGAGGTATTTATACTAACTACAATG
                                                                CDR-2

AGAAGATCAAGGGCGAGGCCACACTGACTGCCGACACATCCTCCAGCACTGCCTACTTGCAG

CTCAGTAGCCTGACATCTGAGGACTCTTTTGTCTATTTCTGTGCAAGGTTTGATGATTTCGA
                                                                                      CDR-3

CCCCTTTTTTGCTTCCTGGGGCCAAGGGACTCTGGTCACTGTCTCTGCA

Protein sequence: (1 letter code)
QVQLQQSGPELVRPGTSVKISCKASGYTFTNYWLGWVKQRPGHGLEWIGDIFPGGIYTNYNE
                                   CDR-1                                                  CDR-2

KIKGEATLTADTSSSTAYLQLSSLTSEDSFVYFCARFDDFDPFFASWGQGTLVTVSA
                                                         CDR-3

*Light chain:*
Nucleotide sequence:
GATGTTTTGATGACCCAAACTCCACTCTCCCTGCCTGTCAGTCTTGGAGATCAAGCCTCCAT CTCTTGCAGATCTAGTCAGACCATTGTACATAGTAATGGAAACACCTATTTAGAATGGTACC
                                                       CDR-1

TGCAGAAACCAGGCCAGTCTCCAAAGCTCCTGATCTACAAAGTTTCCAACCGATTTTCTGGG
                                                                   CDR-2

GTCCCAGACAGGTTCAGTGGCAGTGGATCAGGGACAGATTTCACACTCAATATCAGCAGAGT

GGAGGCTGAGGATCTGGGAATTTATTACTGCTTTCAAAGTTCACGTGTTCCGTACACGTTCG
                                                                         CDR-3

GAGGGGGGACCAAGCTGGAAATAAAA

Protein sequence: (1 letter code)
DVLMTQTPLSLPVSLGDQASISCRSSQTIVHSNGNTYLEWYLQKPGQSPKLLIYKVSNRFSG
                                          CDR-1                                             CDR-2

VPDRFSGSGSGTDFTLNISRVEAEDLGIYYCFQSSRVPYTFGGGTKLEIK
                                    CDR-3

FIGURE 6(continue)

METHOD FOR GENERATING ACTIVE ANTIBODIES AGAINST A RESISTANCE ANTIGEN, ANTIBODIES OBTAINED BY SAID METHOD AND THEIR USES

The present invention relates to a new approach for generating notably monoclonal antibodies, with a therapeutic and/or diagnostic purpose. More particularly, the present invention aims at generating antibodies directed against a tumoral antigen absent at the surface of tumoral cells of native tumors and which would appear after anti-tumoral treatment of these native tumors, an antigen which would also be possibly involved in the resistance of the tumors to these anti-tumoral treatments. The invention also comprises such antibodies as well as the use of these antibodies as a drug for prophylactic and/or therapeutic treatment of resistant tumors. The invention finally comprises compositions comprising such antibodies which may be associated with anti-cancer agents and their use for preventing and/or treating certain cancers.

The discovery of antibodies and more particularly the development of methods for generating antibodies consisted in a revolution in therapeutic treatment or diagnosis and more specifically within the scope of cancer. Indeed, for the first time, this new tool provided the possibility of a targeted treatment because of the intrinsic recognition property of antibodies. A major challenge of these last decades has consisted of developing methods for generating antibodies, whether these are polyclonal antibodies in a first phase, monoclonal antibodies or even fragments of antibodies or analogous structures.

To this day, several technologies have been developed by one skilled in the art in order to be able to generate antibodies with a therapeutic and/or diagnostic purpose.

The oldest antibodies consist in polyclonal antibodies, i.e. heterogeneous populations of antibodies contained in immunized animal serums. To do this, several animals (mice, rats, rabbits, goats, . . . ) are immunized by injection of a given natural or synthetic antigen, in combination with one or more adjuvants, such as Freund's adjuvant and aluminium hydroxide, aiming at promoting and enhancing immune response. The animals are then bled and a serum or anti-serum containing both antibodies which more or less effectively recognize several epitopes of the antigen (polyclonal antibodies), and other antibodies of the animal, is recovered. Purification of the obtained antibodies is carried out for example by affinity chromatography purification.

A first development consisted in generating monoclonal antibodies which may be prepared from hybridomas according to the technique described by KOHLER and MIELSTEIN (1975). This technique enables specific monoclonal antibodies of a predetermined antigen to be generated and consists of merging a clone of a lymphocyte B with a myelomatous cell so as to obtain a cell called a hybridoma. This hybridoma not only has the characteristic of being immortal but also of permanently producing monoclonal and therefore monospecific antibodies.

Other techniques based on the same principle have also been described such as the trioma technique or even still the hybridoma technique described by KOZBOR et al. (1983).

These techniques, initially applied to generating murine antibodies have progressed resulting in the generation of humanized or even human chimeric antibodies. All these techniques are well known today to one skilled in the art.

Human antibodies may be obtained by using the technology of genetically modified mice, a so-called <<xenomouse>> technology as described in patents U.S. Pat. Nos. 5,814,318 and 5,939,598.

Other recent methods have also been developed for generating human monoclonal antibodies and more particularly fragments of antibodies, such as techniques using banks or libraries of phages as described by RIDDER et al. (1995) or the so-called <<phage display>> technology based on extraction of mRNA from a directory of human cells stemming from peripheral blood, the building of a cDNA bank or library comprising the sequences of variable regions, and on insertion of cDNAs into phages in order to produce the variable regions of the antibodies as fragments, preferentially Fab fragments.

Although these methods are different, they all have the same characteristic, i.e of immunizing with a known antigen or, within the scope of libraries or banks, screening these banks with this same known and defined antigen.

The present invention differs from these methods by no longer using a known and defined antigen but directly all or part of a tumor. More particularly, the present invention is directed to the direct use of a lysate and/or a suspension and/or a milled cell homogenate from a tumor. In treating cancer, it has been observed for several years that a certain number of patients which, after having developed a complete and satisfactory response following a first therapeutic treatment, tend to have a relapse. More particularly, it is known that tumors are capable of modifying their genotype and/or their phenotype in order to resist different treatments which are applied to them.

This phenomenon exists both for radiotherapy, chemotherapy type treatments and for treatments with monoclonal antibodies.

Historically, the first chemotherapy compounds for treating cancer were the subject of clinical trials in the 1940s. These were mainly agents with a short half-life such as corticosteroids, antifolates or even vinca alcaloids. However, even when complete remission was achieved, the latter did not generally last for more than a year and systematic relapse was observed, a relapse associated with resistance to the chemotherapy compound used for the treatment (Lehnert M., Eur. J. Cancer, 1996, 32A:912-920).

In response to this phenomenon, performing so-called <<combination>> treatments was contemplated by using various anti-tumoral compounds. Better results were actually obtained by the simultaneous or sequenced use of different compounds. Indeed, in the case of the use of different anti-tumoral compounds each having cyclotoxic activity but different action mechanisms, a tumoral cell resistant to a compound may still be sensitive to at least one of the other compounds used.

However, in spite of using different anti-tumoral compounds or agents, the resistance of tumors remains a major problem within the scope of chemotherapy treatments. The use of combinations has the effect of delaying the occurrence of resistance phenomena but does not cause them to disappear. Resistance to chemotherapies, either related to the initial treatment or appearing upon relapse after a favorable initial response, occurs in practically all the so-called <<curable>> cancers.

As an example, Patent Applications WO 2005/077385, WO 2004/026293 or even WO 2004/110497 may be mentioned, which well illustrate this search for new methods for controlling resistance phenomena, all these applications being based on the principle of an additional injection of a novel generally chemical molecule.

Other mechanisms for acquiring resistance in a tumor initially sensitive to a treatment have been demonstrated. The most widely recognized assumption implies that this resistance phenomenon would result from spontaneous and randomly performed accumulations of somatic mutations in the genotype of the tumoral cell (Cancer Chemotherapy and Biotherapy: Principles and practice, Chabner & Lango editors, 1996, chapter 1).

Another known and described resistance phenomenon, called <<MDR>> (MultiDrug Resistance) is based on the capacity of the tumoral cell of surviving at lethal concentrations of a large amount of pharmacologically, chemically or even structurally different cytotoxic compounds. The cells exhibiting <<MDR>> have a reduction of intracellular accumulation of cytotoxic compounds resulting from the expulsion of said compounds by transport proteins. These proteins, called <<multi-drug transporters>> are membrane proteins capable of expulsing a large range of toxic molecules from the cell. These <<multi-drug transporters>> belong to the <<ATP-binding cassette (ABC) superfamily>> of transport proteins which use the hydrolysis energy of ATP for their activity. Several mechanisms have been shown to be responsible for this <<MDR>>. The most known and most documented gene imparting such a resistance related to an expulsion mechanism depending on ATP is the MDR1 gene.

Concurrently to these resistance phenomena induced by a chemotherapy treatment, an induced resistance was also described, following a treatment with a monoclonal antibody. This resistance may be related to the nature of the host, to pharmacological considerations or else it may be intrinsic to the actual tumor.

Firstly, with the first uses of antibodies related to murine antibodies, the result was an antibody response against said murine antibodies, a so-called HAMA (Human Anti-Mouse Antibody) response. This form of resistance related to the host was in part settled by no longer using murine, but human or humanized antibodies.

Different tests with such human or humanized antibodies demonstrated new phenomena through which the tumor may resist immunological treatments. These new mechanisms are mainly based on mutations induced at the tumor, on constitutive activation of receptors subsequent to a cleaving (or shedding) or even a loss of expression of the targeted antigen.

As this is apparent from Example 1 hereafter, studies conducted by the Applicant for example show that with anti-IGF-1R, EGFR and Her/2neu tritherapy, it is possible to considerably reduce tumoral growth of A549 cells in Nude mice until total disappearance of the tumors occurs in 90% of the treated animals. Although this multiple therapy is significantly more effective than monotherapy or bitherapy it seems that tumors which had nevertheless completely regressed, gradually reappear in spite of continuation of the treatment: they have become resistant to multiple treatment.

From this observation, the Applicant for the first time contemplates direct use of such resistant tumors for generating antibodies, preferentially therapeutic and/or diagnostic monoclonal antibodies, capable of recognizing antigens, the expression of which would be induced at the surface of the tumoral cells of this tumor resistant to anti-tumoral treatment, and which would not be expressed at the surface of the tumoral cells of the native (untreated) tumor, these antigens may also be involved in resistance of the tumor to anti-tumoral treatments.

According to a first aspect, the object of the present invention is therefore the use of a milled homogenate and/or a suspension and/or a cell lysate from a tumor resistant to at least one anti-tumoral compound for immunizing and generating an antibody, or one of its functional fragments, in vitro, directed against a tumoral antigen expressed at the surface of the tumoral cells of said resistant tumor, this tumoral antigen being preferably not expressed at the surface of the tumoral cells of the native tumor from which the resistant tumor stems, this tumoral antigen being possibly involved in the resistance of said tumor to the anti-tumoral compound.

By the expression <<milled homogenate>> or <<cell homogenate>>, is meant a mixture of cells and/or cell fragments stemming from tumors (xenografts, orthotopic grafts, syngeneic grafts, surgical specimens from treated patients in which a tumoral recurrence occurs or from cell cultures) obtained by mechanical dissociation, as for example with a <<Potter>> type, ultrasonic mill, Ultraturax® type, mill etc.

By the expression <<suspension>> or <<cell suspension>>, is meant a suspension of cells obtained after culture in vitro in the presence or absence of treatment and detached from their support by enzyme solutions or non-enzymatic dissociation solutions.

By the expression <<lysate>> or <<cell lysate>>, is meant a mixture of cells and/or cell fragments stemming from tumors (xenografts, orthotopic grafts, syngeneic grafts, surgical specimens from treated patients in which tumoral recurrence occurs or cell cultures) obtained by enzymatic dissociation.

By <<resistant tumor>>, is meant a tumor which does not respond or no longer responds to treatment(s) which is(are) applied. As described above, such a resistance may be observed whether it is after a chemotherapy, radiotherapy, hormonotherapy treatment or even by the particular use of antibodies, these treatments may be applied in an isolated way or else as combinations. Various mechanisms, either known or unknown to this day, may be at the origin of this resistance capability. Finally, this resistance may be expressed by a loss or reduction of the effect of the initially applied treatment.

Of course, the known and described <<escape>> phenomena are part of the resistance phenomena which the invention seeks to control.

By native tumor (or parent tumor), is meant here the designation of the tumor from which the resistant tumor stems, the native tumor having not undergone any anti-tumoral treatment as opposed to the resistant tumor.

Tumoral antigen is meant to refer here in particular to antigens expressed at the surface of the tumoral cells, whether they stem from the native tumor or from the resistant tumor, this tumoral antigen not being expressed at the surface of healthy cells. These tumoral antigens generally are natural macromolecules (which may be synthesized) to which an antibody may be specifically bound. The tumoral antigen may notably be a polypeptide, a polysaccharide, a carbohydrate, a nucleic acid, a lipid, a haptene, or any other compound naturally present at the tumoral cell surface.

Finally, the expressions of "antibody" or "immunoglobulin" are used here interchangeably in their widest sense and comprise monoclonal antibodies (for example whole or intact monoclonal antibodies), polyclonal antibodies, multivalent antibodies, multispecific antibodies (for example bispecific antibodies provided that they show the desired biological activity). Chimeric or humanized antibodies are also included in this designation.

More particularly, such a molecule consists in a glycoprotein comprising at least two heavy chains (H) and two light chains (L) connected together by disulfide bridges. Each heavy chain consists of a heavy chain variable region (or domain) (HCVR or VH) and of a heavy chain constant region. The constant region of the heavy chain comprises three domains CH1, CH2 and CH3. Each light chain consists of a light chain variable region (LCVR or VL) and of a light chain constant region. The constant heavy chain region comprises a LC domain. The VH and VL regions may be subdivided into hypervariability regions called CDRs (Complementary Determining Regions>>), inserted with more preserved regions, called framework regions (FR). Each VH and VL consists of three CDRs and four FRs, arranged from the terminal aminoacid to the terminal carboxy in the following order: FR1, CDR1, FR2, CDR2, FR3, CDR3, FR4. The variable regions of the heavy and light chains comprise a binding domain which interacts with an antigen. The constant regions of the antibodies may mediate binding of immunoglobulin to host tissues or factors, including the different cells of the immune system (for example effector cells) and the first component (Clq) or the system of the standard complement.

They may also cover certain antibody fragments (an expression described in more details) showing the desired affinity and specificity with regard to the source or the type of immunoglobulin (IgG, IgE, IgM, IgA, etc.).

As a rule, for preparing monoclonal antibodies or their functional fragments, notably of murine origin, reference may be made to techniques which are in particular described in the handbook <<Antibodies>> (Harlow and Lane, Antibodies: A Laboratory Manual, Cold Spring Harbor Laboratory, Cold Spring Harbor N.Y., pp. 726, 1988) or to the preparation technique from hybridomas described by Kohler et Milstein (Nature, 256:495-497, 1975).

Among the antibodies which one seeks to generate according to the present invention, antibodies as defined above are preferred and so-called <<active>> antibodies, i.e. having an anti-tumoral activity targeting tumoral cells which resist therapy.

Among the antibodies which one seeks to generate according to the present invention and in a particular aspect of the invention, antibodies as defined above are preferred and those capable of also exerting an anti-tumoral activity directed against tumoral cells with an aggressive phenotype which naturally (before a treatment) express the antigen against which these antibodies are directed.

In a first embodiment, the use according to the invention is characterized in that said resistant tumor is directly obtained by biopsy and/or surgery on a patient who is following or has followed a therapeutic treatment with said at least anti-tumoral compound capable of inducing resistance or for which a resistance of the tumor is ascertained.

In this embodiment, a treatment adapted to each patient may be contemplated in the sense that antibodies are generated according to the invention in response to an immunization carried out with all or part of a resistant tumor stemming from the actual patient. An ex vivo customized therapy of a patient may thereby be contemplated.

In a second embodiment, the use according to the invention is characterized in that said resistant tumor is induced by grafting a tumor line and/or all or part of a human tumor on an animal and then by treating this animal by administration, notably by injection, of at least one anti-tumoral compound for which it is desired to induce or ascertain a resistance.

More particularly, said at least one anti-tumoral compound is selected from chemotherapy agents such as chemical molecules or even therapeutic antibodies or even radiotherapy agents.

Generally in the whole of the present description, an <<anti-tumoral agent>> or an <<anti-cancer therapeutic agent> are meant to designate a substance which, when it is administered to a patient, treats or prevents development of cancer in the patient.

As a non-limiting example for such agents, so-called <<cytotoxic>> agents such as <<alkylating>> agents, anti-metabolites, anti-tumoral antibiotics, mitotic inhibitors, chromatin function inhibitors, anti-angiogenesis agents, anti-estrogens, anti-androgens, or immunomodulators may be mentioned.

Such agents are for example mentioned in the 2006 edition of VIDAL, at the page dedicated to compounds related to cancerology and haematology in the <<Cytotoxics>> column, these cytotoxic compounds mentioned by reference to this document are mentioned here as preferred cytotoxic agents.

The <<alkylating agents>> refer to any substance which may couple covalently with or alkylate any molecule, preferentially a nucleic acid (e.g.: DNA), within a cell. As examples of such alkylating agents, nitrogen mustards may be mentioned such as mechlorethamine, chlorambucil, melphalan, chlorhydrate, pipobroman, prednimustine, disodium phosphate or estramustine; oxazaphosphorines such as cyclophosphamide, altretamine, trofosfamide, sulfofosfamide or ifosfamide; aziridines or ethylene-imines such as thiotepa, triethyleneamine or altetramine; nitrosoureas such as carmustine, streptozocin, fotemustine or lomustine; alkyl sulfonates such as busulfan, treosulfan or improsulfan; triazenes such as dacarbazine; or even platinum complexes such as cisplatinum, oxaliplatinum or carboplatinum.

<<Anti-metabolites>> refer to substances which block growth and/or cell metabolism by interfering with certain activities, notably DNA synthesis. As an example of an antimetabolite, methotrexate, 5-fluorouracil, floxuridine, 5-fluorodeoxyuridine, capecitabine, cytarabine, fludarabine, cytosine arabinoside, 6-mercaptopurine (6-MP), 6-thioguanine (6-TG), chlorodeoxyadenosine, 5-azacytidine, gemcitabine, cladribine, deoxycoformycine and pentostatin.

<<Anti-tumoral antibiotics>> refer to compounds which may prevent or inhibit DNA, RNA and/or protein synthesis. Examples of such anti-tumoral antibiotics comprise doxorubicin, daunorubicin, idarubicin, valrubicin, mitoxantrone, dactinomycin, mithramycin, plicamycin, mitomycin C, bleomycin, and procarbazine.

<<Mitotic inhibitors>> prevent normal progression of the cellular cycle and mitosis. Generally inhibitors of microtubules or <<taxoïds>> such as paclitaxel and docetaxel are capable of inhibiting mitosis. Vinca alkaloids such as vinblastin, vincristin, vindesin and vinorelbin are also capable of inhibiting mitosis.

<<Chromatin function inhibitors>> or <<topo-isomerase inhibitors>> refer to substances which inhibit normal function of the chromatin-modeling proteins such as topo-isomerases I and II. Examples of such inhibitors comprise, for topo-isomerase I, camptothecin as well as its derivatives such as irinotecan or topotecan and for topo-isomerase II, etoposide, etiposide phosphate and teniposide.

<<Anti-angiogenesis agents>> refer to any drug, compound, substance or agent which inhibits growth of blood vessels. Examples of anti-angiogenesis agents comprise, without any limitation, razoxin, marimastat, batimastat, prinomastat, tanomastat, ilomastat, CGS-27023A, halofuginone, COL-3, neovastat, BMS-275291, thalidomide, CDC 501, DMXAA, L-651582, squalamine, endostatin, SU5416, SU6668, alpha-interferon, EMD121974, interleukin-12, IM862, angiostatin and vitaxin.

<<Anti-estrogens>> or <<anti-estrogenic agents>> refer to any substance which reduces, antagonizes or inhibits the action of oestrogens. Examples of such agents are tamoxifen, toremifen, raloxifene, droloxifene, iodoxyfene, anastrozole, letrozole, and exemestane.

<<Anti-androgens>> or <<anti-androgen agents>> refer to any substance which reduces, antagonizes or inhibits the action of an androgen. Examples of anti-androgens are flutamide, nilutamide, bicalutamide, spironolactone, cyproterone acetate, finasteride and cimitidine.

Immunomodulators are substances which stimulate the immune system. Examples of such immunomodulators comprise interferon, interleukins such as aldesleukin, OCT-43, denileukin diflitox or interleukin-2, tumoral necrosis factors such as tasonermin, or other types of immunomodulators such as lentinan, sizofiran, roquinimex, pidotimod, pegademase, thymopentin, poly I:C, or levamisole in combination with 5-fluorouracil.

For more details, one skilled in the art may refer to the handbook edited by the Association Fraçnaise des Enseignants de Chimie Thérapeutique entitled <<traité de chimie thérapeutique, Vol. 6, Médicaments antitumoraux et perspectives dans le traitement des cancers, édition TEC & DOC, 2003>>.

As anti-tumoral agents, radiotherapy, hormonotherapy, or therapy agents targeted by small molecules such as tyrosine kinase inhibitors, may also be mentioned. Finally, according to a preferred embodiment, the antibodies are part of the anti-tumoral agents, which may be used according to the invention. More particularly, mention may be made, as a non-limiting example, of the following antibodies: anti-EGFR antibodies such as cetuximab (C225 or erbitux), matuzumab, huR3, HuMax-EGFR or panitumab; anti-VEGF antibodies such as bevacizumab (Avastin) or 2C3; anti-IGF-IR antibodies such as 7C10, h7C10, hEM164, ABX-IGF-1R, Mab 39, 1H7 or 4G11; anti-HER2 antibodies such as trastuzumab (Herceptin) or pertuzumab; anti-CD20 antibodies as commerituximab, ibritumomab or tositumomab; anti-CD33 antibodies such as gemtuzumab or lintuzumab; anti-CD22 antibodies such as epratuzumab; anti-CD52 antibodies such as alemtuzumab; anti-EpCAM antibodies such as edrecolomab, Ch 17-1A or IGN-101; anti-CTP21 or 16 antibodies such as Xactin; anti-DNA-Ag antibodies such as $^{131}$I-Cotara TNT-1; anti-MUC1 antibodies such as pemtumomab or R1150; anti-MUC18 antibodies such as ABX-MA1; anti-GD3 antibodies such as mitumomab; anti-CEA antibodies such as CeaVac or labetuzumab; anti-CA125 antibodies such as OvaRex; anti-HLA-DR antibodies such as apolizumab; anti-CTLA4 antibodies such as MDX-010; anti-PSMA antibodies such as MDX-070, $^{111}$In & $^{90}$Y-J591, $^{177}$Lu J591, J591-DM1; anti-Lewis Y antibodies such as IGN311; anti-angiogenesis antibodies such as AS1405 and $^{90}$YmuBC1; anti-Trail-R1 antibodies such as TRAIL R1mAb or TRAIL R2mAb; or even any antibody directed against a tyrosine kinase receptor other than those mentioned above or RON, cMET, CXCR 2, CXCR4, Ephrin type receptors, etc., similarly for targeted therapies using small chemical molecules, such as the inhibitors of tyrosine kinase.

Of course, this list by no means limiting but has simply the purpose of mentioning the antibodies used or being developed to this day.

According to a particular embodiment of the invention, it is contemplated that said resistant tumor is resistant to several treatments or anti-tumoral agents, whereby the latter may be of varied nature.

More particularly, the use according to the invention is characterized in that said at least one anti-tumoral compound consists of at least two, preferentially of at least three compounds of different nature and/or having different action mechanisms and/or targeting different proteins.

By different action mechanism, is meant for example that the anti-tumoral agents will alter different biological functions of the cell such as angiogenesis, DNA synthesis or even mitosis.

Targeting of different proteins more particularly refers to the case when anti-tumoral agents are antibodies capable of binding to proteins or receptors of different nature.

Quite obviously, either only combining the antibodies with each other, or only chemotherapy agents with each other or combining both of these families of compounds with each other or with radiotherapy, hormonotherapy treatments or targeted therapies using small chemical molecules as described above, may be contemplated.

Although preferred, it is also not required that the whole of the anti-tumoral compounds all have a different action mechanism or target.

According to a second aspect, the object of the present invention is a method for generating in vitro an antibody, or one of its functional fragments, directed against a tumoral antigen expressed at the surface of a tumor resistant to at least one anti-tumoral compound, said tumoral antigen preferably not being expressed at the surface of the tumoral cells of the corresponding native (untreated) tumor, and said tumoral antigen being possibly involved in the resistance of said tumor resistant to anti-tumoral treatment, the method comprising a step consisting of immunizing animals directly with a milled homogenate and/or a suspension, and/or a cell lysate, from said resistant tumor, and a step consisting of selecting the antibodies which recognize the resistant tumor and not the native tumor from which stems the resistant tumor.

According to a particular aspect of this method of the invention, a method is described for generating in vitro an antibody or one of its functional fragments, directed against a tumoral antigen expressed at the surface of a resistant tumor being possibly involved in the resistance of said resistant tumor, this method consisting of immunizing animals directly with a milled homogenate and/or a suspension and/or a cell lysate, from said tumor resistant to at least one anti-tumoral compound (anti-tumoral compound for which resistance of the tumor was ascertained or for which it is desired to induce resistance), after either tolerization of the animals or not, with a milled homogenate and/or a suspension and/or a cell lysate from a native tumor (a tumor not having been the subject of any treatment). This tolerization, which is performed with an immunosuppressive agent of the cyclophosphamide type, has the purpose of canceling the immune response directed against all surface antigens present before the anti-tumoral treatment(s) applied to the animal or human with the purpose of inducing resistance or within the scope of a therapy as regards humans. Thus, the immune response subsequent to administration, notably an injection of preparations from resistant tumors, will be focused on the structures of surfaces induced by the treatment and potentially involved in establishing tumor resistance. The efficiency of tolerization is evaluated by following the disappearance of the serum titer established following immunization of the animals with tumoral cells from the native tumor.

The spleens of the mice immunized according to the method above will then be sampled and the splenocytes fused with myeloma cells according to the standard process known to one skilled in the art.

Screening of the obtained hybridomas following this cell fusion, will be carried out by <<differential immunohistochemistry>> on slides prepared beforehand and bearing cuts of (untreated) <<native tumors>> or cuts of resistant tumors (either monotreated or polytreated with anti-tumoral agents). Only the hybridomas producing antibodies which recognize the resistant tumor and not the native tumors will be selected, cloned and frozen in order to produce the antibodies and to test them for their anti-tumoral activity. The whole of this method is schematized in FIGS. 2 and 3 later on. It should be noted that such an approach may also be contemplated for searching and identifying intracellular resistance molecules.

The antibodies as defined above, according to the present invention, are preferably specific, notably murine, chimeric or humanized monoclonal antibodies which may be obtained according to standard methods well known to one skilled in the art.

Generally for preparing monoclonal antibodies or their functional fragments, notably of murine origin, reference may be made to the techniques which are in particular described in the handbook <<Antibodies>> (Harlow and Lane, Antibodies: A Laboratory Manual, Cold Spring Harbor Laboratory, Cold Spring Harbor N.Y., pp. 726, 1988) or to the preparation technique from hybridomas described by Kohler and Milstein (Nature, 256:495-497, 1975).

Chimeric or humanized antibodies are also included as antibodies according to the present invention.

A chimeric antibody is meant to designate an antibody which contains a natural variable (light chain and heavy chain) region derived from an antibody of a given species in association with constant light chain and heavy chain regions of an antibody of a species heterologous to said given species (mice, horses, rabbits, dogs, cows, hens, etc.).

The antibodies or their chimeric type fragments according to the invention may be prepared by using genetic recombination techniques. For example, the chimeric antibody may be produced by cloning a recombinant DNA including a promoter and a sequence coding for the variable region of a non-human, notably murine monoclonal antibody, according to the invention, and a sequence coding for the human antibody constant region. A chimeric antibody of the invention coded by such a recombinant gene will for example be a mouse-human construct, the specificity of this antibody being determined by the variable region derived from murine DNA and its isotypes determined by the constant region derived from human DNA. For the methods of preparation of chimeric antibodies, reference may for example be made to the document Verhoeyn et al. (BioEssays, 8:74, 1988), Morrison et al. (Proc. Natl. Acad. Sci. USA 82:6851-6855, 1984) or U.S. Pat. No. 4,816,567.

A humanized antibody is meant to designate an antibody which contains CDR regions derived from an antibody of non-human origin, the other portions of the antibody molecule being derived from one (or more) human antibody(ies). Additionally, some of the residues of the segments of the skeleton (named FR) may be changed in order to retain the binding affinity (Jones et al., Nature, 321:522-525, 1986; Verhoeyen et al., Science, 239:1534-1536, 1988; Riechmann et al., Nature, 332:323-327, 1988).

The humanized antibodies according to the invention or their fragments may be prepared by techniques known to one skilled in the art (such as for example those described in the documents Singer et al., J. Immun. 150:2844-2857, 1992; Mountain et al., Biotechnol. Genet. Eng. Rev., 10:1-142, 1992; or Bebbington et al., Bio/Technology, 10:169-175, 1992).

Other humanization techniques are also known to one skilled in the art such as for example the <<CDR Grafting>> technique described by PDL, being the subject of patents EP 0 451 261, EP 0 682 040, EP 0 939 127, EP 0 566 647 or even U.S. Pat. Nos. 5,530,101, 6,180,370, 5,585,089 and 5,693, 761. U.S. Pat. No. 5,639,641 or even U.S. Pat. Nos. 6,054, 297, 5,886,152 and 5,877,293 may also be mentioned.

A functional fragment of an antibody according to the invention, is meant to designate in particular an antibody fragment, such as fragments Fv, scFv (sc for simple chain), Fab, F(ab')$_2$, Fab', scFv-Fc or diabodies, or any fragment for which the lifetime would have been increased by chemical modification, like adding poly(alkylene) glycol such as polyethylene glycol <<PEGylation>> or by incorporation in a lysosome. Said fragment generally has at least one of the characteristic CDRs of the antibody from which it stems and is capable of generally exerting the even partial activity of the antibody from which it stems.

Preferably, said functional segments will consist of or comprise a partial sequence of the heavy or light variable chain of the antibody from which they are derived, said partial sequence being sufficient in order to retain the same binding specificity as the antibody from which it stems and sufficient affinity, preferably at least equal to $\frac{1}{100}$, more preferably at least $\frac{1}{10}$ of that of the antibody from which it stems.

Such a functional fragment will include a minimum of 5 amino acids, preferably 10, 15, 25, 50 and 100 consecutive amino acids of the sequence of the antibody from which it stems.

Preferably, these functional fragments will be fragments of the Fv, scFv, Fab, F(ab')$_2$, F(ab'), scFv-Fc type or diabodies, which generally have the same binding specificity as the antibody from which they stem. According to the present invention, antibody fragments of the invention may be obtained from antibodies such as described earlier, by methods such as digestion by enzymes, such as pepsin or papain and/or by cleaving the disulfide bridges by chemical reduction. In another way, the antibody fragments comprised in the present invention may be obtained by techniques of genetic recombinations also well-known to one skilled in the art or even by peptide synthesis, e.g. by means of automatic peptide synthesizers such as those provided by Applied Biosystems, etc.

More preferably, the invention comprises antibodies, or their functional fragments according to the present invention, notably chimeric or humanized ones obtained by genetic recombination or by chemical synthesis.

According to a preferred embodiment of the method according to the invention, said immunization is performed by intraperitoneal and/or subcutaneous and/or intravenous and/or intra-splenic injection. As each immunization mode may be interchangeable, selection of one mode relatively to the other is performed according to the animals used and to the knowledge and practices of one skilled in the art.

More particularly, according to a first embodiment, the resulting tumor is obtained directly by biopsy and/or surgery of a patient following, or having followed, a therapeutic treatment with at least one anti-tumoral compound capable of inducing resistance or for which resistance was ascertained.

According to a second embodiment, the resistant tumor is induced by grafting a tumor line and/or whole or part of a human tumor on an animal and then by treating this animal by injecting at least one anti-tumoral compound for which it is desired to induce a resistance or to ascertain a resistance.

Whichever the preferred embodiment above, the method according to the invention is characterized in that said active antibody, or one of its functional fragments, consists in a monoclonal antibody.

More particularly, said monoclonal antibody or one of its functional fragments consists in an immunoglobulin selected from the group of an IgG, an IgA, an IgM, an IgD or an IgE.

Even more preferably, said monoclonal antibody or one of its functional fragments consists in an IgG of gamma 1, gamma 2 or gamma 4 isotype.

Nevertheless, it should be understood that according to the invention immunoglobulins of type IgG1 and IgG2 are preferred because of their property of inducing effector functions.

Generally, one skilled in the art will recognize that effector functions comprise as a non-limiting example, binding to C1q, CDC (complement-dependent cytotoxicity), binding to the Fc receptor, ADCC (antibody-dependent cellular cytotoxicity) and phagocytosis.

More particularly, the preferred effector functions according to the invention are ADCC and CDC.

Generally, the functional fragments to which the invention refers, are selected from fragments Fv, Fab, (Fab')$_2$, Fab', scFv, scFv-Fc and diabodies, or any fragment for which the lifetime would have been increased, like pegylated fragments.

In a more specific but by no means limiting way, the method according to the invention comprises at least the following steps:

i) directly immunizing animals with a milled homogenate and/or a suspension and/or a cell lysate stemming from a resistant tumor, ii) fusing cells of the spleen of the animal immunized in step i) with myeloma cells so as to obtain hybridomas, and iii) selecting by differential selections, the hybridomas secreting antibodies which specifically recognize the antigens expressed at the surface of the tumoral cells of the resistant tumor and the expression of which is induced by the anti-tumoral treatment.

By <<differential selection>>, is meant any selection based on methods with which the induced antigens may be distinguished by the occurrence of resistance to a treatment relatively to the antigens present on the cells before establishment of this resistance.

As a non-limiting example of a technique providing such <<differential selection>>, mention may be made of immunohistochemistry on frozen cuts or included in paraffin or of approaches of the <<protein arrays>> or <<gene arrays>> type.

More particularly, use of the so-called <<tissue array>> technique is preferred. The <<tissue array>> technique consists of building from blocks of tissues included in paraffin or frozen, new blocks containing several tens to several hundreds of cores of these tissues so as to be able, after cutting these blocks of <<tissue arrays>>, to mount microscope slides comprising several tens to several hundreds of cuts of tissues.

According to a preferred embodiment, the method according to the invention further comprises prior to step i) described above, the following steps:

a) selecting and grafting on animals, a tumor line and/or whole or part of a so-called <<native>> tumor, b) treating a portion of these grafted animals with at least one anti-tumoral compound, c) recovering whole or part of the so-called <<native>> tumors from the untreated animals grafted in step a), d) recovering whole or part of the resistant tumors from the animals treated in step b), e) preparing a means for differential selection of the antibodies from the tumors, entirely or partly recovered in steps c) and d), respectively, and f) preparing a mild homogenate and/or a cell lysate from the resistant tumors, entirely or partly recovered in step d).

In the present description, it should be understood that the expressions <<native tumors>> and <<parent tumors>> are equivalent and will be used indifferently.

According to an embodiment of the invention, said tumor line and/or so-called <<native>> tumor are selected from the group of tumor cells (A549) from the lungs but also in a non-limiting way, from the colon, the prostate, the breasts, the ovaries, or any tumor for which resistances to treatments are ascertained.

Additionally, an anti-tumoral compound used according to the invention, is selected from chemotherapy agents, radiotherapy agents, chemical molecules or antibodies, the whole of these different compounds being as defined above in the present description.

According to a preferred embodiment of the invention, said at least one anti-tumoral compound consists of a monoclonal antibody, said monoclonal antibody being even more preferably selected from the group of antibodies, or their functional fragments, directed against growth factor receptors, molecules involved in angiogenesis, or even chemokines and integrins involved in cell migration phenomena.

By <<growth receptors>>, is meant any transmembrane protein which, following the binding of ligand(s) or an independent change in ligand conformation, or homo- or hetero-dimerizations with other membrane proteins, will mediate a proliferative response. By <<molecules involved in angiogenesis>>, is meant any membrane receptor which, following the binding of ligand(s) or an independent change in ligand conformation or homo- or hetero-dimerizations with other membrane proteins, will result in the formation of vessels.

By <<chemokines and integrins involved in cell migration phenomena>>, is meant any soluble molecule capable of having an activity of digesting extracellular matrices and/or a chemo-attractive activity.

According to another embodiment of the invention, the method is characterized in that said at least one anti-tumoral compound consists of a combination of at least two, preferentially at least three anti-tumoral compounds of different nature and/or having different action mechanisms and/or targeting different proteins.

Preferably, said combination of anti-tumoral compounds consists in a combination of monoclonal antibodies or their functional fragments.

Still more preferably, said combination of monoclonal antibodies or of its functional fragments, consists in a combination of antibodies selected from anti-IGF-IR, anti-EGFR, anti-Her/2neu, anti-VEGF, anti-VEGFR, anti-CXCR, anti-cMET, anti-RON, Ephrin, antibodies, etc.

According to an embodiment, as a non-limiting example, the method according to the invention is characterized in that said combination consists in the combination of an anti-IGF-IR antibody, of an anti-EGFR antibody and of anti-Her/2neu antibody, said mentioned antibodies preferably consisting of the monoclonal antibodies 7C10, 225 and h4D5, respectively.

The monoclonal antibody 7C10 consists of the antibody described in the patent application WO 03/059951 filed by the Applicant on Jan. 20, 2003 and the contents of which are incorporated here by reference.

The monoclonal antibody called 7C10 is secreted by the hybridoma deposited at the Collection Nationale de Cultures De Microorganismes (CNCM), Institut Pasteur, 25, rue du Cocteur Roux, F-75724, PARIS Cedex 15, (France) on Sep. 19, 2001, under the number I-2717. Please note that the depository CNCM is an International Depository Authority (IDA) under the Budapest Treaty located in France.

The deposited hybridoma was accepted by an IDA under the terms of the Budapest Treaty, and all restrictions upon public access to the deposited material will be irrevocably removed upon the grant of a patent in the present application.

The monoclonal antibody 225 consists of the antibody produced by the hybridoma deposited at the ATCC under reference HB-8508.

The monoclonal antibody h4D5 consists of commercially available herceptin, for example at the ICR (Institut Claudius Regaud).

According a further preferred embodiment, the method according to the invention is characterized in that said step iii) for selecting hybridomas secreting antibodies which do not recognize the antigens of the so-called <<native>> tumor cell is performed by differential screening between the tissue of the untreated so-called <<native>> tumor and that of the resistant tumor and/or tumor made to be resistant.

By <<differential screening>>, is meant a screening with which the induced antigens may be distinguished by the occurrence of a resistance to a treatment relatively to the antigens present on the cells before establishment of this resistance. Preferably, differential screening is performed by applying the means obtained in step e) as described above.

Finally, according to a last embodiment of the invention, it is preferred that the method comprise an additional tolerization step prior to step i).

By <<tolerization>>, is meant extinction of an immune response induced by means of immunosuppressive compounds such as cyclophosphamide. In practice, said tolerization step may consist of:
- administering, notably by injection to the animals, a milled homogenate and/or a suspension and/or a cell lysate obtained from so-called native tumors stemming from step c), and
- treating these animals with an immunosuppressor in order to eliminate B cells activated by the injection of the step above and thereby inhibit any potential response against said so-called native tumor.

Of course, any similar method or practice, or with which the same result may be obtained, should be considered as equivalent and comprised in the scope of the invention. By <<immunosuppressor>>, is meant any substance capable of depleting cell populations of the immune system. As a non-limiting example, cyclophosphamide may be mentioned.

In another aspect, the present invention relates to a method for generating and selecting in vitro an antibody or one of its functional fragments, capable of inhibiting resistance of a tumor to an anti-tumoral compound or to a method for generating and selecting in vitro an antibody or one of its functional fragments, directed against a tumoral antigen expressed at the surface of a tumor resistant to at least one anti-tumoral compound, said tumoral antigen being involved in the resistance of said tumor to the anti-tumoral compound, characterized in that the method comprises:
a) a method for generating in vitro an antibody, or one of its functional fragments, according to the invention, said antibody being directed against said tumoral antigen specifically expressed at the surface of the resistant tumor, said tumoral antigen not being expressed at the surface of the cells of the native tumor from which the resistant tumor stems;
b) putting the antibody obtained in step a) in vitro or in vivo in contact with the tumor resistant to the anti-tumoral compound; and
c) selecting said antibody if an inhibiting effect of this antibody on the resistance of the tumor to the anti-tumoral compound is demonstrated.

According to another embodiment, a test may be conducted in vitro or in vivo with the purpose of defining whether the antigen for which expression is induced by the anti-tumoral treatment is involved in the resistance phenomenon or not. According to a preferred embodiment, such a step may consist of testing in vitro or in vivo the antibody obtained according to the invention on the resistant tumor and observing whether a resistance-inhibiting activity is developed on the resistant tumor.

Still another aspect, the present invention relates to a method for generating and selecting in vitro an antibody, or one of its functional fragments, capable of exerting an anti-tumoral activity, notably inhibiting the proliferation of tumoral cells expressing the antigen against which said antibody is directed, characterized in that the method comprises:
a) a method for generating in vitro an antibody, or one of its functional fragments, according to the invention, said antibody being directed against said tumoral antigen specifically expressed at the surface of the resistant tumor, said tumoral antigen not being expressed at the surface of the cells of the native tumor from which the resistant tumor stems;
b) putting the antibody obtained in step a) in vitro or in vivo in contact with a tumor, the cells of which express said tumoral antigen, preferably with said resistant tumor used in step a) or with a tumor having an aggressive phenotype; and
c) selecting said antibody if an anti-tumoral effect is demonstrated on this tumor, notably inhibition of cell proliferation of this tumor.

In step b) of the method hereinbefore, it should be understood that the tumor, the cells of which express said tumoral antigen, is not necessarily the tumor resistant to the anti-tumoral compound having been used for generating said antibody. Any tumor notably with an aggressive phenotype, the tumoral cells of which express the tumoral antigen recognized by said antibody may be used in step b).

The invention is also obviously directed to the use of a method as described above for generating therapeutic and/or diagnostic monoclonal antibodies. The invention also covers the partial use of such a method which may be developed by one skilled in the art in order to meet a particular criterion or else quite simply to differ from the present description. According to a third aspect of the invention, a monoclonal antibody or one of its functional fragments, obtained by applying the method according to the invention as described above, are contemplated.

The present invention is innovative in the sense that no antibody to this day has been described as having such properties, more so as having been obtained by such a method.

Preferably, said functional fragments according to the present invention will be selected from the Fv, scFv, Fab, (Fab')$_2$, Fab', scFv-Fc fragments or diabodies, or any functional fragment for which the lifetime would have been increased by chemical modification, notably by PEGylation, or by incorporation into a liposome. Of course, this list is by no means limiting or any other type of fragment known to one skilled in the art should be considered as being part of the invention.

As an illustrative example of the invention, 5 antibodies obtained by applying the method according to the invention are described hereafter. These antibodies called 1A6, 1A9, 2E11, 3C11 and 3G7 may be murine, chimeric or humanized.

According to a first embodiment, the present invention is directed to a monoclonal antibody, or one of its functional fragments, characterized in that it comprises:
- a light chain comprising the CDR regions of sequences SEQ ID Nos. 1, 2 and 3, or for which the sequences have at least 80% identity after optimum alignment with the sequences SEQ ID Nos. 1, 2 and 3; and
- a heavy chain comprising CDR regions of sequences SEQ ID Nos. 4, 5 and 6, and for which the sequences have at least 80% identity after optimum alignment with the sequences SEQ ID Nos. 4, 5 and 6.

In the present description, the terms of polypeptides, polypeptide sequences, peptides and proteins attached to the antibody compounds or their sequences, are interchangeable.

It should be understood here that the invention does not relate to antibodies in the natural form, i.e. there are not taken in their natural environment but it was possible to isolate or obtain them by purification from natural sources, or else obtain them by genetic recombination, or by chemical synthesis, and they may then include non-natural amino acids as this will be described later on.

CDR region(s) or CDR (s) are meant to designate hypervariable regions of heavy and light chains of immunoglobulins as defined by Kabat et al. (Kabat et al., Sequences of proteins of immunological interest, $5^{th}$ Ed., U.S. Department of Health and Human Services, NIH, 1991, and later editions). There are 3 heavy chain CDRs and 3 light chain CDRs. The term CDR or CDRs is used here in order to designate depending on the cases, one of these regions or several of them, or even the whole of these regions which contain the majority of the amino acid residues responsible for affinity binding of the antibody for the antigen or the epitope which it recognizes.

<<Identity percentage>> between two sequences of nucleic acids or amino acids in the sense of the present invention is meant to designate a percentage of nucleotides or identical amino acids residues between both sequences to be compared, obtained after best alignment (optimum alignment), this percentage being purely statistical and differences between both sequences being randomly distributed and over all their length. Comparison of sequences between two sequences of nucleic acids or amino acids are traditionally performed by comparing these sequences after having aligned them in an optimum way, said comparison may be performed by segment or through a <<comparison window>>. The optimum alignment of the sequences for the comparison may be performed, as well as manually, by means of the local homology algorithm of Smith and Waterman (1981) [Ad. App. Math. 2:482], by means of the local homology algorithm of Neddleman et Wunsch (1970) [J. Mol. Biol. 48:443], by means of the similarity search method of Pearson and Lipman (1988) [Proc. Natl. Acad. Sci. USA 85:2444], by means of computer software packages using these algorithms (GAP, BESTFIT, FASTA and TFASTA in the Wisconsin Genetics Software Package, Genetics Computer Group, 575 Science Dr., Madison, Wis., or even by the comparison software packages BLAST N or BLAST P).

The identity percentage between two sequences of nucleic acids or amino acids is determined by comparing these two sequences aligned in an optimum way in which the sequence of nucleic acids or amino acids to be compared may comprise additions or deletions relatively to the reference sequence for an optimum alignment between both sequences. The identity percentage is calculated by determining the number of identical positions for which the nucleotide or the amino acid residue is identical between two sequences, by dividing this number of identical positions by the total number of positions in the comparison window and by multiplying the obtained result by 100 in order to obtain the identity percentage between both of these sequences.

For example, the BLAST program, <<BLAST 2 sequences>>, may be used (Tatusova et al., <<Blast 2 sequences—a new tool for comparing protein and nucleotide sequences>>, FEMS Microbiol. Lett. 174:247-250) available on the site http://www.ncbi.nlm.nih.gov/gorf/bl2.html, the parameters used being those given by default (in particular for the parameters <<open gap penalty>>: 5, and <<extension gap penalty>>: 2; the selected matrix being for example the <<BLOSUM 62>> matrix proposed by the program), the identity percentage between both sequences to be compared being directly computed by the program. It is also possible to use other programs such as <<ALIGN>> or <<Megalign>> (DNASTAR) software packages.

Per amino acid sequence having at least 80%, preferably 85%, 90%, 95% and 98% identity with a reference amino acid sequence, those having, relatively to the reference sequence, certain modifications are preferred, in particular a deletion, addition or substitution of at least one amino acid, a truncation or an extension. In the case of a substitution of one or more consecutive or non-consecutive amino acid(s), substitutions are preferred in which the substituted amino acids are replaced with <<equivalent>> amino acids. The expression <<equivalent amino acids>> here aims at designating any amino acid capable of being substituted for one of the amino acids of the basic structure without however substantially changing the biological activities of the corresponding antibodies and as they will be defined subsequently, notably in the examples.

These equivalent amino acids may be determined either by relying on their structure homology with amino acids which they replace, or on results of comparative tests of biological activity between the different antibodies, which may be conducted.

As a non-limiting example, Table 1 below repeats the possibilities of substitution capable of being carried out without their resulting an extensive change in biological activity of the corresponding modified antibody, inverse substitutions may naturally be contemplated under the same conditions.

TABLE 1

| Original residue | Substitution(s) |
|---|---|
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (G) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

Preferably the antibody described above is named 1A6 and comprises a heavy sequence chain comprising the sequence SEQ ID No. 7 and a light chain comprising the sequence SEQ ID No. 8.

More particularly, the present invention is also directed to the murine hybridoma (1A6) capable of secreting the antibody 1A6 as described above. In the present description, the same code is indifferently used whether one is speaking of the murine hybridoma or else of the antibody produced by this same hybridoma.

Such a murine hybridoma consists of the hybridoma deposited at the CNCM (Collection Nationale de Cultures de Microorganismes), Institut Pasteur, Paris (France) on May 31, 2006 under No. I-3612. Among the six short CDR sequences, the third CDR of the heavy chain (CDRH3) has larger size variability (a larger diversity essentially due to mechanisms for arranging the genes which give rise to it). It may be as short as 2 amino acids while the longest known size is 26. Functionally, CDRH3 plays a separate role in the determination of the specificity of the antibody (Segal et al., PNAS, 71:4298-4302, 1974; Amit et al., Science, 233:747-753, 1986; Chothia et al., J. Mol. Biol., 196:901-917, 1987; Chothia et al., Nature, 342:877-883, 1989; Caton et al., J. Immunol., 144:1965-1968, 1990; Sharon et al., PNAS, 87:4814-4817, 1990; Sharon et al., J. Immunol., 144:4863-4869, 1990; Kabat et al., J. Immunol, 147:1709-1719, 1991).

It is known that only a small percentage of the amino acids of the CDRs contributes to the construction of the binding site of the antibody, but these residues should be kept in a very specific three-dimensional conformation.

According to a second embodiment, the invention is directed to a monoclonal antibody or one of its functional fragments, characterized in that it comprises:
 a light chain comprising CDR regions of sequences SEQ ID Nos. 9, 10 and 11, or for which the sequences have at least 80% identity after optimum alignment with the sequences SEQ ID Nos. 9, 10 and 11; and
 a heavy chain comprising CDR regions of sequences SEQ ID Nos. 12, 13 and 14, or for which the sequences have at least 80% identity after optimum alignment with the sequences SEQ ID Nos. 12, 13 and 14.

According to another embodiment, said antibody according to the invention, named 1A9, comprises a heavy sequence chain comprising the sequence SEQ ID No. 15 and a light chain comprising the sequence SEQ ID No. 16.

According to another aspect, the murine hybridoma (1A9) capable of secreting an antibody as defined above is also claimed.

Finally, according to a preferred embodiment of the invention, the murine hybridoma 1A9 deposited at the CNCM (Collection Nationale de Cultures de Microorganisms), Institut Pasteur, Paris (France) on May 31, 2006 under No. I-3613, is covered.

According to a third embodiment, the invention is directed to a monoclonal antibody or one of its functional fragments, obtained according to the method object of the invention and which comprises:
 a light chain comprising CDR regions with sequences SEQ ID Nos. 17, 18 and 19, or for which the sequences have at least 80% identity after optimum alignment with the sequences SEQ Nos. 17, 18 and 19; and
 a heavy chain comprising CDR regions of sequences SEQ ID Nos. 20, 21 and 22, or for which the sequences have at least 80% identity after optimum alignment with the sequences SEQ ID Nos. 20, 21 and 22.

Preferably, said antibody according to the invention, named 2E11, comprises a heavy sequence chain comprising the sequence SEQ ID No. 23 and a light chain comprising the sequence SEQ ID No. 24.

According to another aspect, the invention also consists in the murine hybridoma 2E11 capable of secreting an antibody as described above.

More particularly, said murine hybridoma consists in the hybridoma deposited at the CNCM (Collection Nationale de Cultures de Microorganisms), Institut Pasteur, Paris (France) on May 31, 2006 under the No. I-3615.

According to a fourth embodiment, the invention is directed to a monoclonal antibody or one of its functional fragments, obtained by a method as described above and which comprises:
 a light chain comprising the CDR regions of sequences SEQ ID Nos. 25, 26 and 27, or for which the sequences have at least 80% identity after optimum alignment with the sequences SEQ ID Nos. 25, 26 and 27; and
 a heavy chain comprising the CDR regions of sequences SEQ ID Nos. 28, 29 and 30, or for which the sequences have at least 80% identity after optimum alignment with the sequences SEQ ID Nos. 28, 29 and 30.

More specifically, said antibody according to the invention, named 3C11, comprises a heavy sequence chain comprising the sequence SEQ ID No. 31 and a light chain comprising the sequence SEQ ID No. 32.

According to another aspect, the invention also relates to the murine hybridoma 3C11 capable of secreting an antibody as described above.

Said hybridoma preferentially consists in the hybridoma deposited at the CNCM (Collection Nationale de Cultures de Microorganisms), Institut Pasteur, Paris (France) on May 31, 2006 under No. I-3614.

Finally, according to a fifth embodiment of the invention, the latter relates to a monoclonal antibody or one of its functional fragments obtained by applying the method object of the present invention and which comprises:
 a light chain comprising CDR regions of sequence SEQ ID No. 33, 34 or 35, or for which the sequences have at least 80% identity after optimum alignment with the sequences SEQ ID Nos. 33, 34 and 35; and
 a heavy chain comprising the CDR regions of sequences SEQ ID No. 36, 37 and 38, or for which the sequences have at least 80% identity after optimum alignment with the sequences SEQ ID Nos. 36, 37 and 38.

Preferably, said antibody named 3G7, comprises a heavy sequence chain comprising the sequence SEQ ID No. 39 and a light chain comprising sequence SEQ ID No. 40.

According to another aspect of the invention, a murine hybridoma 3G7 capable of secreting an antibody as described above is claimed.

Said hybridoma preferentially consists in the murine hybridoma deposited at the la
CNCM (Collection Nationale de Cultures de Microorganismes), Institut Pasteur, Paris (France) on May 31, 2006 under No. I-3616. For the sake of clarity, it is grouped in Table 2 below with the correspondence between the antibodies object of the invention and the respective sequences of amino acids of the CDRs of said antibodies.

TABLE 2

| Antibody | Heavy chain | Light chain | SEQ ID No. |
|---|---|---|---|
| 1A6 | | CDR 1 | 1 |
| | | CDR 2 | 2 |
| | | CDR 3 | 3 |
| | CDR 1 | | 4 |
| | CDR 2 | | 5 |
| | CDR 3 | | 6 |
| 1A9 | | CDR 1 | 9 |
| | | CDR 2 | 10 |
| | | CDR 3 | 11 |
| | CDR 1 | | 12 |
| | CDR 2 | | 13 |
| | CDR 3 | | 14 |
| 2E11 | | CDR 1 | 17 |
| | | CDR 2 | 18 |
| | | CDR 3 | 19 |
| | CDR 1 | | 20 |
| | CDR 2 | | 21 |
| | CDR 3 | | 22 |
| 3C11 | | CDR 1 | 25 |
| | | CDR 2 | 26 |
| | | CDR 3 | 27 |
| | CDR 1 | | 28 |
| | CDR 2 | | 29 |
| | CDR 3 | | 30 |

TABLE 2-continued

| Antibody | Heavy chain | Light chain | SEQ ID No. |
|---|---|---|---|
| 3G7 | | CDR 1 | 33 |
| | | CDR 2 | 34 |
| | | CDR 3 | 35 |
| | CDR 1 | | 36 |
| | CDR 2 | | 37 |
| | CDR 3 | | 38 |

Table 3 herein below represents, as for it, the correspondence between these same antibodies object of the invention and the respective sequences of amino acids of the heavy and light chains of said antibodies.

TABLE 3

| Antibody | Heavy chain | Light chain | SEQ ID No. |
|---|---|---|---|
| 1A6 | Entire | | 7 |
| | | entire | 8 |
| 1A9 | Entire | | 15 |
| | | entire | 16 |
| 2E11 | Entire | | 23 |
| | | entire | 24 |
| 3C11 | Entire | | 31 |
| | | entire | 32 |
| 3G7 | Entire | | 39 |
| | | entire | 40 |

Finally, Table 4 herein below groups the names of each antibody object of the invention with the deposit numbers at the CNCM.

| Hybridoma | CNCM deposit no. |
|---|---|
| 1A6 | I-3612 |
| 1A9 | I-3613 |
| 3C11 | I-3614 |
| 2E11 | I-3615 |
| 3G7 | I-3616 |

Of course, the whole of the properties or modifications described above for the antibody 1A6 are applied to the other antibodies object of the invention and more particularly to the antibodies identified as 1A9, 2E11, 3C11 and 3G7.

In a similar way to what has been described above for any antibody obtained according to the method object of the invention, it is also specified that the whole of the described characteristics, properties or modifications should be considered as also applying to the antibodies identified in the present application.

More particularly, it is specified that any functional fragment is selected from the Fv, Fab, (Fab')₂, Fab', scFv, scFv-Fc fragments and diabodies, or any fragment for which the half-life would have been increased, such as pegylated fragments.

Preferably, the antibody object of the present invention preferentially consists in an antibody, or one of its functional fragments, secreted by one of the hybridomas described above, i.e. hybridomas I3612, I-3613, I-3614, I-3615 or I-3616.

According to a further embodiment of the invention, said antibody is a chimeric antibody and further comprises constant light chain and heavy chain regions derived from an antibody of a species heterologous to mice.

Preferably, said heterologous species is the human species.

Still more preferably, said chimeric antibody, or one of its functional fragments, according to the invention, is characterized in that the light chain and heavy chain constant regions derived from a human antibody are the kappa and, gamma 1, gamma 2 or gamma 4 regions, respectively.

Finally, even more preferably, said antibody consists of a humanized antibody and comprises a light chain and/or a heavy chain in which skeleton segments FR1-FR4 of said light chain and/or heavy chain are derived from skeleton segments FR1-FR4 respectively of a light chain and/or a heavy chain of human antibodies.

In an also particular aspect, the present invention relates to a chimeric antibody, or one of its functional fragments, according to the invention, characterized in that said antibody further comprises light chain and heavy chain constant regions derived from an antibody of a species heterologous to mice, notably humans, and preferably, in that the light chain and heavy chain constant regions derived from a human antibody are the kappa and gamma-1, gamma-2 or gamma-4 regions, respectively.

According to a further aspect of the invention, an isolated nucleic acid is described, characterized in that it is selected from the following nucleic acids:

a) a DNA or ARN nucleic acid, coding for an antibody or one of its functional fragments according to the invention;

b) a nucleic acid complementary to a nucleic acid as defined under a);

c) a nucleic acid of at least 18 nucleotides capable of hybridizing under strong stringency conditions with at least one of the CDRs of sequences SEQ ID Nos. 41-46, 49-54, 57-62, 65-70, 73-78, or with a sequence having at least 80% identity after optimum alignment with the sequences SEQ ID Nos. 41-46, 49-54, 57-62, 65-70, 73-78; and d) a nucleic acid of at least 18 nucleotides capable of hybridizing under strong stringency conditions with at least one of the light chains of sequences SEQ ID Nos. 48, 56, 64, 72 or 80 and/or one of the heavy chains of sequences SEQ ID Nos. 47, 55, 63, 71 or 79, or with a sequence having at least 80% identity after optimum alignment with sequences SEQ ID Nos. 47, 48, 55, 56, 63, 64, 71, 72, 79 or 80. By the terms nucleic acid, nucleic sequence or nucleic acid sequence, polynucleotide, oligonucleotide, polynucleotide sequence, nucleotide sequence, terms which will be used indifferently in the present description, the intention is to designate a specific linking of nucleotides, either modified or not, with which a fragment or a region of nucleic acid may be defined, either including non-natural nucleotides or not and which may correspond both to a double strand DNA, a single strand DNA and transcription products of said DNAs.

It should also be understood here that the present invention does not relate to nucleotide sequences in their natural chromosomal environment, i.e. in the natural condition. These are sequences which have been isolated and/or purified, i.e. they have been sampled directly or indirectly, for example by copying, their environment having been at least partially modified. The intention is also to designate here isolated nucleic acids obtained via genetic recombination by means of host cells for example or obtained by chemical synthesis.

Nucleic sequences having an identity percentage of at least 80%, preferably 85%, 90%, 95% and 98%, after optimum alignment with a preferential sequence, are meant to designate nucleic sequences having relatively to the reference nucleic sequence, certain modifications such as in particular a deletion, a truncation, an extension, a chimeric fusion and/or a notably point-like substitution. These are preferably sequences for which the sequences code for the same sequences of amino acids as the reference sequence, this being related to degeneration of the genetic code, or complementary sequences which are capable of specifically hybridizing with preferential reference sequences under strong stringency conditions notably as defined hereafter.

Hybridization under strong stringency conditions means that the conditions of temperature and of ionic force are selected so as to allow the hybridization to be maintained between two complementary DNA fragments. As an illustration, strong stringency conditions of the hybridization step for the purpose of defining the polynucleotide fragments described above, advantageously are the following.

DNA-DNA or DNA-ARN hybridization is performed in two steps: (1) prehybridization at 42° C. for 3 hours in a phosphate buffer (20 mM, pH 7.5) containing 5×SSC (1×SSC corresponds to a 0.15 M NaCl+0.015 M sodium citrate solution), 50% formamide, 7% sodium dodecyl sulfate (SDS), 10×Denhardt's, 5% dextran sulfate and 1% of salmon sperm DNA; (2) actual hybridization for 20 hours at a temperature depending on the size of the probe (i.e.: 42° C., for a probe with a size >100 nucleotides) followed by two 20-minute washes at 20° C. in 2×SSC+2% SDS, a 20-minute wash at 20° C. in 0.1×SSC +0.1% SDS. The last wash is performed in 0.1×SSC+0.1% SDS for 30 minutes at 60° C. for a probe with a size >100 nucleotides. The strong stringency hybridization conditions, described above for a polynucleotide with a definite size, may be adapted by one skilled in the art to oligonucleotides of larger or smaller size, according to the teaching of Sambrook et al. (1989, Molecular cloning: a laboratory manual. 2nd Ed. Cold Spring Harbor).

For more clarity, the correspondence between the antibodies object of the invention, more particularly the sequences of CDRs as well as variable chains and their nucleotide sequences is also specified in Table 5 below.

TABLE 5

| Antibody | Heavy chain | Light chain | SEQ ID No. |
|----------|-------------|-------------|------------|
| 1A6      |             | CDR 1       | 41         |
|          |             | CDR 2       | 42         |
|          |             | CDR 3       | 43         |
|          | CDR 1       |             | 44         |
|          | CDR 2       |             | 45         |
|          | CDR 3       |             | 46         |
| 1A9      |             | CDR 1       | 49         |
|          |             | CDR 2       | 50         |
|          |             | CDR 3       | 51         |
|          | CDR 1       |             | 52         |
|          | CDR 2       |             | 53         |
|          | CDR 3       |             | 54         |
| 2E11     |             | CDR 1       | 57         |
|          |             | CDR 2       | 58         |
|          |             | CDR 3       | 59         |
|          | CDR 1       |             | 60         |
|          | CDR 2       |             | 61         |
|          | CDR 3       |             | 62         |
| 3C11     |             | CDR 1       | 65         |
|          |             | CDR 2       | 66         |
|          |             | CDR 3       | 67         |
|          | CDR 1       |             | 68         |
|          | CDR 2       |             | 69         |
|          | CDR 3       |             | 70         |
| 3G7      |             | CDR 1       | 73         |
|          |             | CDR 2       | 74         |
|          |             | CDR 3       | 75         |
|          | CDR 1       |             | 76         |
|          | CDR 2       |             | 77         |
|          | CDR 3       |             | 78         |
| 1A6      | entire      |             | 47         |
|          |             | entire      | 48         |
| 1A9      | entire      |             | 55         |
|          |             | entire      | 56         |
| 2E11     | entire      |             | 63         |
|          |             | entire      | 64         |
| 3C11     | entire      |             | 71         |
|          |             | entire      | 72         |
| 3G7      | entire      |             | 79         |
|          |             | entire      | 80         |

The invention also relates to a vector comprising a nucleic acid according to the present invention.

The invention is notably directed to cloning and/or expression vectors which contain a nucleotide sequence according to the invention.

The vectors according to the invention preferably include elements which allow expression and/or secretion of nucleotide sequences in a determined host cell. The vector should then include a promoter, signals for initiating and terminating the translation, as well as suitable regions for regulating the transcription. It should be able to be kept in a stable way in the host cell and may possibly have particular signals which specify the secretion of the translated protein. These different elements are selected and optimized by one skilled in the art depending on the host cell used. For this purpose, the nucleotide sequences according to the invention may be inserted in self-replicating vectors within the selected host, or be integrative vectors of the selected host.

Such vectors are prepared by methods currently used by one skilled in the art, and the resulting clone may be introduced into a suitable host by standard methods, such as lipofection, electroporation, thermal shock, or chemical methods.

The vectors according to the invention for example are vectors of plasmid or viral origin. They are useful for transforming host cells in order to clone and express the nucleotide sequences according to the invention.

The invention also comprises host cells transformed by or comprising a vector according to the invention.

The cell host may be selected from prokaryotic or eukaryotic systems, for example bacterial cells but also yeast cells or animal cells, in particular cells of mammals. Insect cells or plant cells may also be used.

The invention also concerns animals, except humans, which comprise a transformed cell according to the invention.

In another aspect, the object of the invention is a method for producing an antibody or one of its functional fragments according to the invention, characterized in that it comprises the following steps:

a) cultivating in a medium and under suitable culture conditions a host cell according to the invention; and
b) recovering said antibodies, or one of its functional fragments, thereby produced from the culture medium or from said cultivated cells.

The transformed cells according to the invention may be used in methods for preparing recombinant polypeptides according to the invention. The methods for preparing a polypeptide according to the invention in a recombinant form, characterized in that they apply a vector and/or a cell transformed by a vector according to the invention, are themselves comprised in the present invention. Preferably, a cell transformed by a vector according to the invention is cultivated under conditions which allow expression of said polypeptide and said recombinant peptide is recovered.

As this has been stated, the host cell may be selected from prokaryotic or eukaryotic systems. In particular, it is possible to identify nucleotide sequences according to the invention, which facilitate secretion in such a prokaryotic or eukaryotic system. A vector according to the invention bearing such a sequence may therefore be advantageously used for producing recombinant proteins intended to be secreted. Indeed, purification of these recombinant proteins of interest will be facilitated by the fact they are present in the supernatant of the cell culture rather than in the interior of the host cells.

The polypeptides according to the invention may also be prepared by chemical synthesis. Such a preparation method is also an object of the invention. One skilled in the art is aware of chemical synthesis methods, for example techniques applying solid phases (see notably Steward et al., Solid phase peptides synthesis, Pierce Chem. Company, Rockford, 111, $2^{nd}$ ed., (1984)) or techniques using partial solid phases, by condensation of fragments or by synthesis in a standard solution. The polypeptides obtained by chemical synthesis and which may include corresponding non-natural amino acids are also comprised in the invention.

The antibodies, or one of their functional fragments, capable of being obtained by a method according to the invention, are also comprised in the present invention. Bispecific or bifunctional antibodies form a second generation of monoclonal antibodies in which two different variable regions are combined in the same molecule (Hollinger and Bohlen, 1999, Cancer and metastasis rev. 18:411-419). Their utility was demonstrated both in the diagnosis field and in the field of therapy because of their capacity of recruiting new effector functions or of targeting several molecules at the surface of tumor cells. These antibodies may be obtained by chemical methods (Glennie M J et al., 1987, J. Immunol. 139, 2367-2375; Repp R. et al., 1995, J. Hemat. 377-382) or somatic (Staerz U. D. and Bevan M. J., 1986, PNAS 83, 1453-1457; Suresh M. R. et al., 1986, Method Enzymol., 121:210-228) but also and preferentially by genetic engineering techniques with which heterodimerization may be forced and which thereby facilitate the purification method of the sought antibody (Merchand et al., 1998, Nature Biotech., 16:677-681).

These bispecific antibodies may be constructed as entire IgGs, as bispecific Fab'2s, as Fab'PEGs or as diabodies or even as bispecific scFvs but also as a tetravalent bispecific antibody or two binding sites are present for each targeted antigen (Park et al., 2000, Mol. Immunol., 37(18):1123-30) or its fragments as described above.

Besides an economical benefit from the fact that production and administration of a bispecific antibody are less expensive than producing two specific antibodies, the use of such bispecific antibodies has the advantage of reducing the toxicity of the treatment. Indeed, with the use of a bispecific antibody it is possible to reduce the global amount of circulating antibodies and consequently possible toxicity.

In a preferred embodiment of the invention, the bispecific antibody is a bivalent or tetravalent antibody.

In practice, the benefit from using a tetravalent bispecific antibody is that it has larger avidity as compared with a bivalent antibody because of the presence of two binding sites for each target.

In a similar way to selecting functional fragments of the antibody described above, said second pattern is selected from Fv, Fab, (Fab')$_2$, Fab', Fab'PEG, scFv, scFv-Fc fragments and diabodies, or any form for which the life-time would have been increased.

In still another aspect, the object of the invention is an antibody or one of its functional fragments, according to the invention as a drug, preferably a humanized antibody as defined hereinbefore. By antibody, is meant in the following of the present description, both an antibody obtained by applying the method of the invention as described above, and an antibody selected from the identified and named antibodies 1A6, 1A9, 2E11, 3C11 or even 3G7.

The invention also relates to a pharmaceutical composition comprising as an active ingredient, a compound consisting in an antibody, or one of its functional fragments, according to the invention, preferably added with a pharmaceutically acceptable excipient and/or carrier.

More particularly, the invention covers a composition comprising as an active ingredient, a compound consisting in an antibody, or one of its functional fragments, such as described above, or produced by the hybridoma I-3612, I-3613, I-3614, I-3615 or I-3616.

According to still another embodiment, the present invention also relates to a pharmaceutical composition as described above which further comprises as a combination product for simultaneous, separate use, or extended over time, of a chemotherapy agent, radiotherapy agent or an antibody. By <<simultaneous use>>, is meant the administration of both compounds of the composition according to the invention comprised in a single and same pharmaceutical form.

By <<separate use>>, is meant the administration at the same time of both compounds of the composition according to the invention, comprised in distinct pharmaceutical forms.

By <<use extended over time>> is meant the successive administration of both compounds of the composition according to the invention, each comprised in a distinct pharmaceutical form. By chemotherapy agent, is meant any compound entering the definition and the list appearing above in the present description and being an integral part of the invention.

In a particularly preferred embodiment, said composition as a combination product according to the invention is characterized in that said cytotoxic agent is chemically coupled with said antibody for simultaneous use.

In a particularly preferred embodiment, said composition according to the invention is characterized in that said cytotoxic/cytostatic agent is selected from agents which inhibit or stabilize the spindle, preferably vinorelbine and/or vinflunine In order to facilitate coupling between said cytotoxic agent and said antibody according to the invention, spacer molecules may notably be introduced between both compounds to be coupled, such as polyalkylene glycols such as polyethylene glycol, or even amino acids, or in another embodiment, active derivatives of said cytotoxic agents may be used, in which functions will have been introduced, capable of reacting with said antibody according to the invention. These coupling techniques are well known to one skilled in the art and will not be developed in the present description.

The invention in another aspect relates to a composition characterized in that at least one of said antibodies, or one of their functional fragments, is conjugate with a cell toxin and/or a radioelement.

Preferably, said toxin is a toxin from enterobacteria, notably exotoxin A from *Pseudomonas*.

Toxin or radioelement conjugate with at least one antibody, or one of their functional fragments, according to the invention, is meant to designate any means with which said toxin or said radioelement may be bound to said at least one antibody, notably by covalent coupling between both compounds, with or without introducing a binding molecule. Another form of coupling may consist in the use of an ion chelator providing non-covalent complexation, such as for example EDTA, DOTA or even a complex of the $^{99m}$Tc type.

Also preferably, said at least one antibody forming said conjugate according to the invention, is selected from its functional fragments, notably the fragments severed from their component Fc such as scFv fragments.

The present invention further comprises the use of the composition according to the invention for preparing a drug.

The object of the present invention is also the use of an antibody as described above, or even obtained by the method object of the invention and also described above, for preparing a drug intended for preventing or treating cancer.

The object of the present invention is also the use of an antibody as described above, or even obtained with the method object of the invention and also described above, for preparing a drug intended to inhibit the resistance of a tumor to an anti-tumoral treatment in a patient within the scope of preventing and treating cancer in this patient.

Preferably, said cancer is a cancer of a resistant type selected from colon, prostate, breast, lung, ovary or pancreas cancers.

According to another embodiment of the invention, the use of an antibody or one of its functional fragments according to the invention is also claimed for preparing a drug intended for specifically targeting a biologically active compound towards resistant tumors and/or which are in a late stage. The marked antibodies according to the invention or their functional fragments for example include so-called immunoconjugate antibodies which may be for example conjugated with enzymes such as peroxidase, alkaline phosphatase, α-D-galactosidase, glucose oxidase, glucose amylase, carbonic anhydrase, acetyl-cholinesterase, lysozyme, malate dehydrogenase or glucose-6 phosphate dehydrogenase or with a molecule such as biotin, digoxigenin, or 5-bromo-deoxyuridine. Fluorescent markers may also be conjugated with the antibodies or their functional fragments according to the invention, and notably include fluorescein and its derivatives, fluorochromium, rhodamine and its derivatives, GFP (Green Fluorescent Protein), dansyl, umbelliferone etc. In such conjugates, the antibodies of the invention or their functional fragments may be prepared by methods known to one skilled in the art. They may be coupled with enzymes or fluorescent markers directly or via a spacer group or a binding group such as a polyaldehyde, such as glutaraldehyde, ethylene diamine tetraacetic acid (EDTA), diethylene triamine pentaacetic acid (DPTA), or in the presence of coupling agents such as periodate, etc. The conjugates including fluorescein type markers may be prepared by reaction with an isothiocyanate.

Other conjugates may also include chemiluminescent markers such as luminol and dioxetanes, bioluminescent markers such as luciferase and luciferin, or even radioactive markers.

A biologically active compound is meant to designate here any compound capable of modulating, of notably inhibiting cell activity, in particular their growth, their proliferation, gene transcription or translation.

In the present description, a pharmaceutically acceptable vehicle is meant to designate a compound or a combination of compounds entering a pharmaceutical composition which does not cause secondary reactions and with which administration of the active compound(s) may for example be facilitated, its life-time and/or its effectiveness in the organism may be increased, its solubility in solution may be increased, or even its preservation may be improved. These pharmaceutically acceptable carriers are well known and will be adapted by one skilled in the art depending on the nature and the administration method of the selected active compound(s).

Preferably, these compounds will be administered systemically, in particular via an intravenous route, via an intramuscular, intradermal, intraperitoneal or subcutaneous route, or orally. More preferably, the composition comprising the antibodies according to the invention will be administered repeatedly, spread out over time.

Their methods of administration, dosage forms and optimum galenic forms may be determined according to the criteria generally taken into account in establishing a treatment adapted to a patient, as for example the age or the body weight of the patient, the seriousness of his/her condition, the tolerance to the treatment and the reported secondary effects.

Other features and advantages of the invention will appear in the description which follows, with the examples and figures including the captions, which are illustrated hereafter.

Finally, according to a last aspect of the invention, the use of the method according to the invention is contemplated for identifying new therapeutic and/or diagnostic, intra- or extracellular targets, involved in resistance phenomena.

Finally, said method for identifying new therapeutic and/or diagnostic, intra- or extra-cellular targets, involved in resistance phenomena is characterized in that it consists of applying the method according to the invention as described above in order to obtain a monoclonal antibody and then identify the compound, in particular the protein recognized by said monoclonal antibody.

Such an identification of a compound, notably of a protein, may be performed by any technique known to one skilled in the art, such as for example immunoprecipitation and/or immunopurification of cell lysate and protein identification by Western-blot techniques coupled with standard proteomic techniques.

The captions of the figures and examples which follow are intended to illustrate the invention without limiting by any means the scope thereof.

CAPTIONS OF THE FIGURES

FIG. 1: FIG. 1 illustrates the time course of the tumor volume following h4D5, 225 and 7C 10 tritherapy and shows the occurrence of a resistance to such a treatment.

Figure 2:
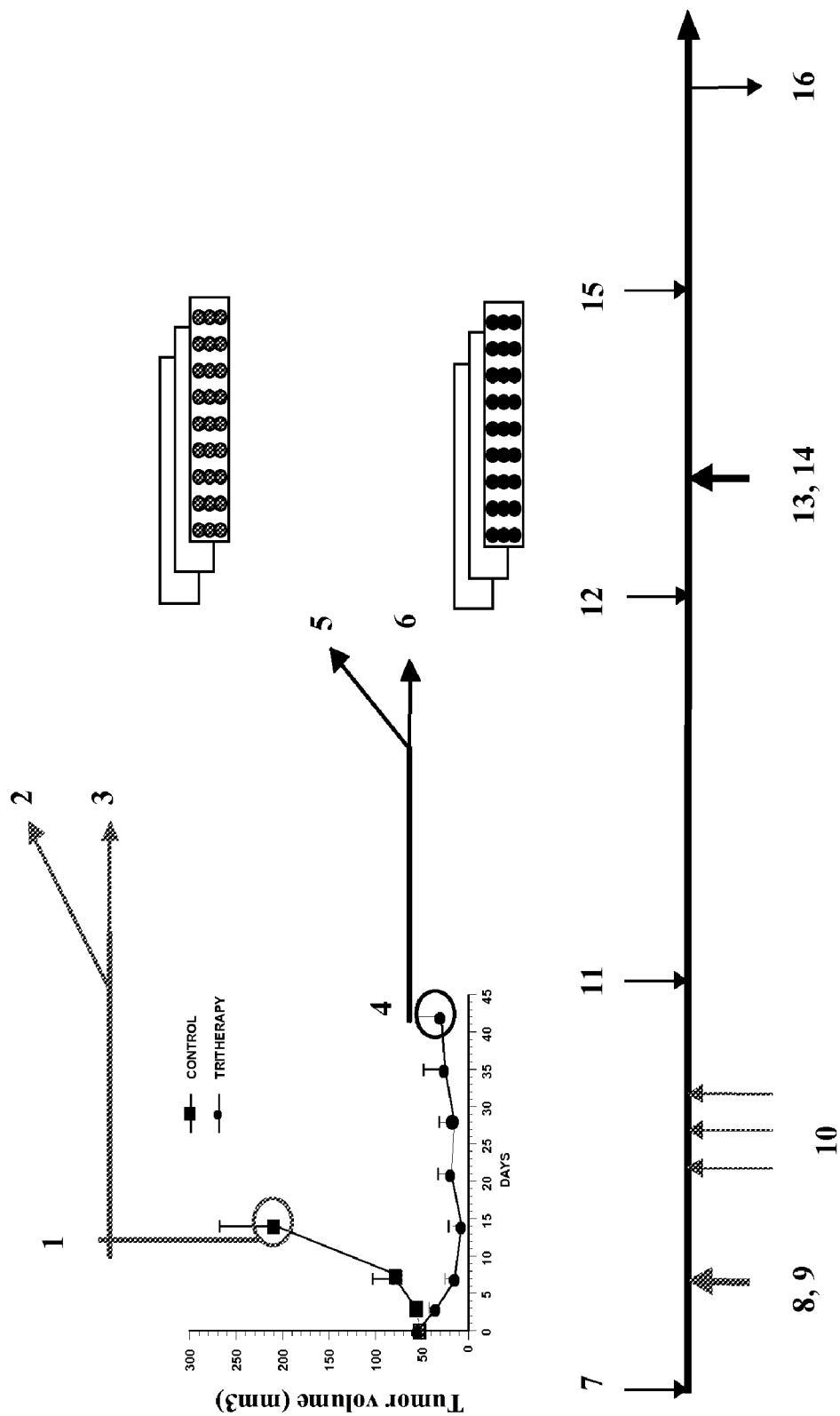

FIG. 2: FIG. 2 illustrates, in a first illustrative form, an explanatory diagram of an embodiment of the invention.

1: Sampling of control tumors, division into two portions.

2: Tolerization of the mice. Preparation of the cells for the immunization: lysate, cellular suspension, etc. Tolerization by i.p. injection of cyclophosphamide or another tolerizing agent.

3: Slides for IHC screening: freezing or inclusion of the tumors. Preparation of the slides for labelling=negative control slides.

4: Sampling of resistant tumors, division into two portions.

5: Preparation of the cells for immunization: lysate, cell suspension, etc.

6: Freezing or inclusion of the tumors: Preparation of the slides for labeling=test slides.

7: Sampling of the control tumors.

8: Immunization of the mice: cell preparation from control tumors.

9: Control IHC slides.

10: Tolerization by injection(s) of an immunosuppressive agent.

11: Sampling of the sera for checking lack of response against native cells.

12: Sampling of the resistant tumors.

13: Immunization of tolerized mice: cell preparation from resistant tumors.

14: Test IHC slides.

15: Sampling of the sera for the labeling of IHC tumors versus resistant tumors.

16: Selection of hybridomas: absence of labeling on the control tumor slides, positive labeling on the resistant tumors (absence of labeling on the stromal cells, labeling of tumoral cells).

Figure 3:
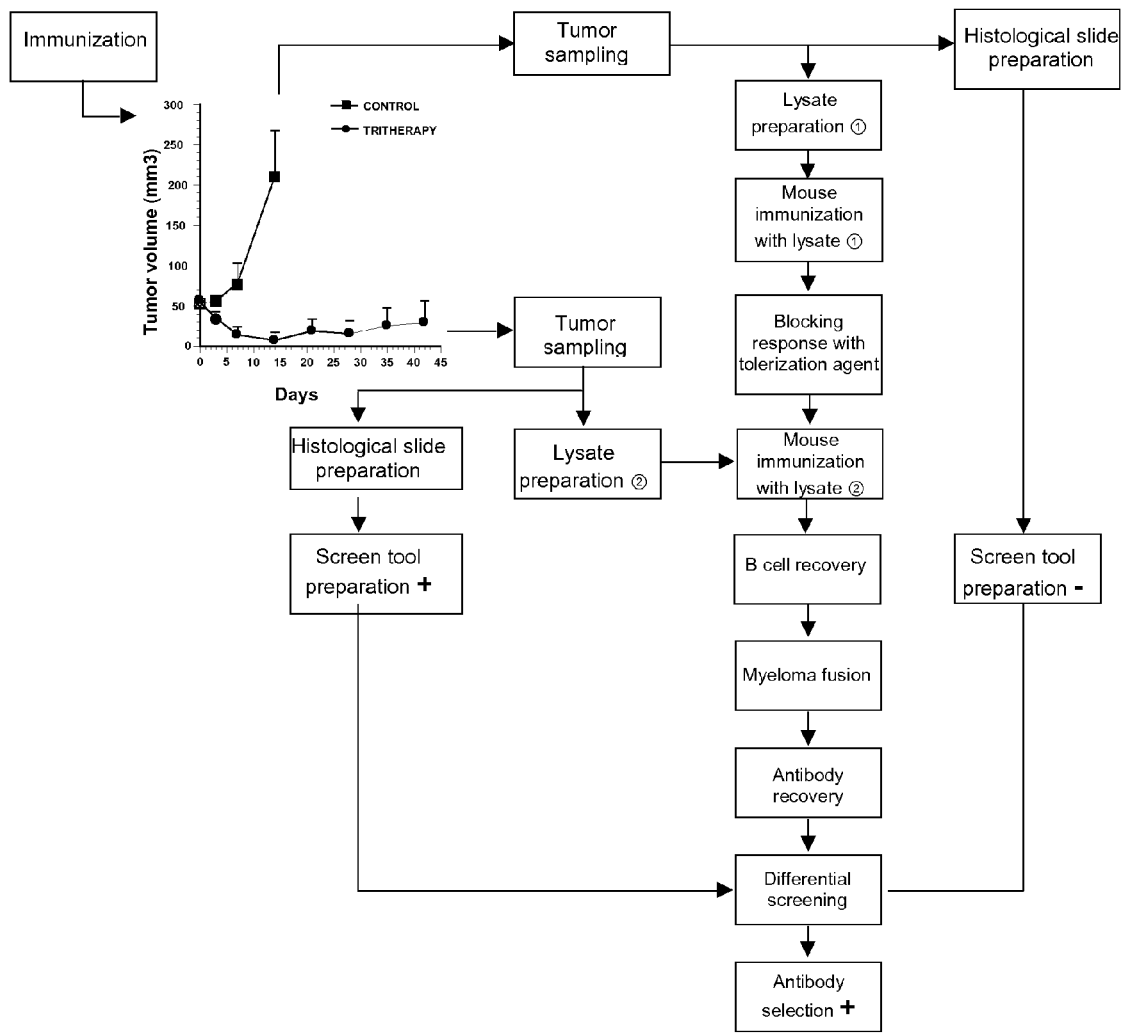

FIG. 3: FIG. 3 also illustrates, but this time as a diagram, an embodiment of the method according to the invention.

FIG. 4: FIG. 4 illustrates the profile of the antibodies according to the invention on slides of the <<tissue array>> type generated from tumors which have been used for tolerization and immunizations.

Figure 5:
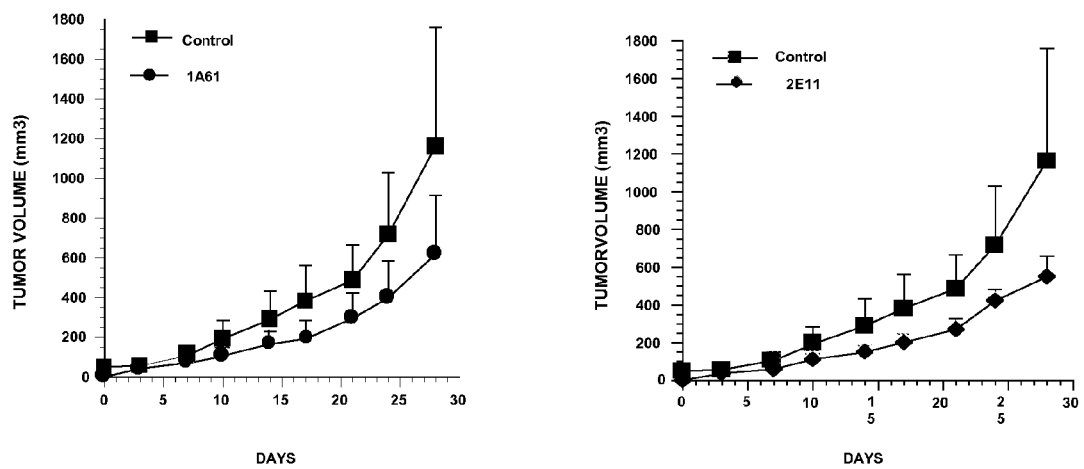

FIG. 5: FIG. 5 illustrates the evaluation of the anti-tumoral activity of the antibodies 1A6 and 2E11 in the colon xenograft model HT29.

FIG. 6: FIG. 6 shows the respective sequences of heavy and light chains of the antibodies 1A6 (SEQ ID NOS: 47, 7, 48, and 8), 1A9 (SEQ ID NOS: 55, 15, 56, and 16), 2E11 (SEQ ID NOS: 63, 23, 64, and 24) 3C11 (SEQ ID NOS: 71, 31, 72, and 32) and 3G7SEQ ID NOS: 79, 39, 80, and 40). The respective CDRs appear underlined and in bold characters.

Figure 7:
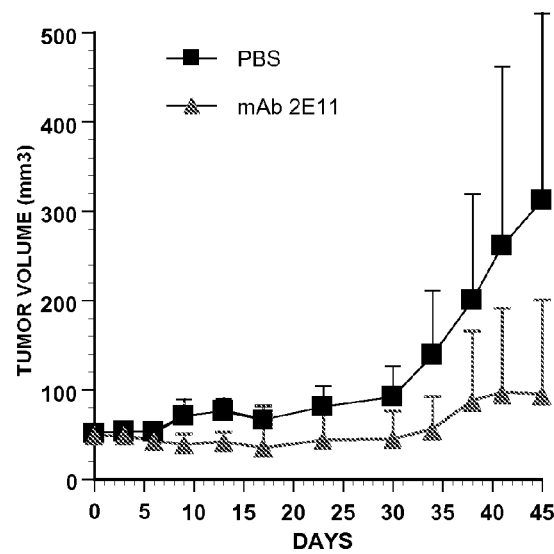

FIG. 7: FIG. 7 illustrates the evaluation of the anti-tumoral activity of the antibody 2E11 in the pancreas xenograft model BxPC3.

EXAMPLE 1

Demonstrating Resistance of a Tumoral Cell A549 to Anti-IGF-IR, EGFR and Her/2neu Tritherapy A549 cells were grafted on mice. When the tumor is installed, the mice are treated twice a week with a mixture containing 300 µg of each of the following antibodies, i.e; h4D5 (herceptin provided by ICR, Institut Claude Regaud, service pharmacie, 20-24, rue du Pont Saint-Pierre, 31052 Toulouse), 225 (ATCC No. HB-8508) and 7C10.

As soon as the first week of treatment, a regression of the tumor growth, until total disappearance of the tumor, may be observed in certain mice. The treatment is maintained in spite of total or partial regression of the tumor.

Subsequently, reappearance of the tumors is observed in spite of the continuity of the treatment, which indicates that tumors resistant to tritherapy have been generated.

An example is illustrated in FIG. 1 which shows tumor regression until day 15 and reappearance of the tumors from day 15 indicating development of resistance.

EXAMPLE 2

Generation of Active Monoclonal Antibodies Directed Against an Antigen Involved in the Resistance to a Combined Anti-IGF-1R, EGFR and Her/2neu Therapy A549 cells are grafted in two batches of 10 mice. The first batch receives biweekly injections of PBS. The second batch is treated with a combination of antibodies (7C10, 225 and h4D5) directed against the IGF-1R, EGFR and Her/2neu receptors, respectively. This combination of antibodies causes tumor regression resulting in the disappearance of the tumors in 60% of the treated animals. In spite of this drastic effect, the tumors recur in all the animals.

A549 tumors are recovered in animals treated with PBS when they attain 100-200 mm$^3$.

Each of these tumors is divided into two portions: one is cryofrozen with the purpose of generating immunohistochemistry slides of the <<tissue array>> type, the other one is used for tolerizing BALB/c mice. This tolerization is performed by intraperitoneal injection of a milled homogenate of cells from the tumor followed by administration of cyclophosphamide and has the purpose of totally eradicating the response directed against the untreated <<parent>> A549 tumors. During this tumor recurrence, tumors are also sampled when they reach a volume between 100 and 200 mm$^3$. They are then divided into two equal portions. One portion will be cryofrozen with the purpose of generating immunohistochemistry slides of the <<tissue array>> type as described above for PBS control tumors. A milled homogenate will be prepared with the second portion and will be used for immunizing the mice tolerized beforehand with the untreated A549 tumors. These mice all in all received 3 intraperitoneal injections of milled homogenates of tumors resistant to tritherapy, adjuvated by complete Freund's adjuvant for the first injection and by incomplete Freund's adjuvant for the following injections.

Cell fusion is then carried out and the hybridomas resulting from this fusion, are screened in immunohistochemistry on <<tissue array>> type slides prepared beforehand.

The hybridomas secreting antibodies recognizing the resistant tissues, and recognizing neither the tumors from the control batch PBS nor the native A549 cell which was used for establishing the tumor in vivo, are cloned and frozen. The antibodies are then produced in ascite liquid, purified, retested in immunohistochemistry before being tested in vivo on cells expressing a surface structure or antigen recognized by the antibodies (these cells were selected beforehand by FACSCAN analysis of a non-exhaustive panel of tumor lines available for each antibody).

FIG. 4 shows the profile of the retained antibodies.

Table 6 below as for it, groups the cells recognized by these antibodies (Recognition of the antibodies selected in histology with the FACSCAN instrument, of different cell lines).

TABLE 6

| Hybridoma | Clone | Isotype | In vivo model |
|---|---|---|---|
| 1A6 | C7 | IgM k | MCF7/Colo205 |
|  | D10 |  | LnCap/HT29 |
| 1A9 | E11 | IgG1 k | HepG2/H69/LnCap |
|  | F1 |  |  |
| 2E11 | A2 | IgG1 k | HT29/BxPC3/H69 |
|  | B11 |  |  |
| 2E11 | A8 | IgG1 k | HT29/BxPC3/H69 |
|  | B9 |  |  |
| 3C11 | E8 | IgM k | Colo205 |
|  | E9 |  |  |
| 3G7 | A7 | IgM | DU145 |
|  | B2 |  |  |

EXAMPLE 3

Evaluation of the Anti-Tumoral Activity of the Antibodies Generated According to the Invention (More Particularly 1A6 and 2E11) in a Colon Xenograft Model HT29

$5.10^6$ HT29 cells are grafted on <<Swiss-Nude>> mice. Five days after the grafting, the tumors are measurable and the mice are divided into three batches of six mice with tumors of homogenous size. The mice are either treated with PBS (negative control) or with 0.5 mg of antibody 1A6 or 2E11, three times a week (a first presenting dose injection: 1 mg/mouse).

Tumor volume tracking is carried out twice a week, knowing that the tumor volume is conventionally computed according to the following formula: $(\pi/6) \times (1) \times (L) \times (e)$, with 1=measured width, L=measured length and e=measured thickness.

The results are illustrated in FIG. 5.

HT29 cells may be considered as being of an aggressive phenotype. The obtained results demonstrate the possibility of using antibodies directly against antigens of tumor cells stemming from the tumor treated by an anti-tumoral composition (see Example 2) and resistant thereto, as an anti-tumoral compound for treating tumors with an aggressive phenotype.

The results obtained in this experiment validate the original approach of generating antibodies and the concept of generating antibodies for a therapeutic purpose from resistance induced in mice. This method may be applied to any other combination of drugs, including chemotherapy drugs, either alone or combined together or with antibodies or with inhibitors of tyrosine kinase or with proteasome inhibitors, by proceeding in the same way.

EXAMPLE 4

Evaluation of the Anti-Tumoral Activity of the Antibody 2E11 Generated According to the Invention in Pancreas Xenograft Model BxPC3

$10.10^6$ BxPC3 cells are grafted on athymic "Nude" mice. Five days after the grafting, the tumors are measurable and the mice are divided into two batches of six mice with tumors of homogenous size. The mice are either treated with PBS (negative control) or with the antibody 2E11 (1 mg/dose), two times a week. Tumor volume tracking is carried out twice a week.

The results are illustrated in FIG. 7.

The results obtained in this experiment validate the functional activity of the antibody 2E11 and also the concept of generating antibodies for a therapeutic purpose from resistance induced in mice.

| | | |
|---|---|---|
| 0-1 | Form PCT/RO/134 (SAFE) Indications Relating to Deposited Microorganism(s) or Other Biological Material (PCT Rule 13bis) | |
| 0-1-1 | Prepared Using | PCT Online Filing Version 3.5.000.193 MT/FOP 20020701/0.20.5.9 |
| 0-2 | International Application No. | |
| 0-3 | Applicant's or agent's file reference | 351656D24754 |
| 1 | The indications made below relate to the deposited microorganism(s) or other biological material referred to in the description on: | |
| 1-1 | page | p25, p52 |
| 1-2 | line | 113, 114 |
| 1-3 | Identification of deposit | |
| 1-3-1 | Name of depositary institution | CNCM Collection nationale de cultures de micro-organismes |
| 1-3-2 | Address of depositary institution | Institut Pasteur, 28, rue du Dr Roux, 75724 Paris Cedex 15, France |
| 1-3-3 | Date of deposit | 31 May 2006 (31.05.2006) |
| 1-3-4 | Accession Number | CNCM I-3612 |
| 1-5 | Designated States for Which Indications are Made | all designations |
| 2 | The indications made below relate to the deposited microorganism(s) or other biological material referred to in the description on: | |
| 2-1 | page | p26, p52 |
| 2-2 | line | 127, 130 |
| 2-3 | Identification of deposit | |
| 2-3-1 | Name of depositary institution | CNCM Collection nationale de cultures de micro-organismes |
| 2-3-2 | Address of depositary institution | Institut Pasteur, 28, rue du Dr Roux, 75724 Paris Cedex 15, France |
| 2-3-3 | Date of deposit | 31 May 2006 (31.05.2006) |
| 2-3-4 | Accession Number | CNCM I-3613 |
| 2-5 | Designated States for Which Indications are Made | all designations |
| 3 | The indications made below relate to the deposited microorganism(s) or other biological material referred to in the description on: | |
| 3-1 | page | p27, p54 |
| 3-2 | line | 131, 13 |
| 3-3 | Identification of deposit | |
| 3-3-1 | Name of depositary institution | CNCM Collection nationale de cultures de micro-organismes |
| 3-3-2 | Address of depositary institution | Institut Pasteur, 28, rue du Dr Roux, 75724 Paris Cedex 15, France |
| 3-3-3 | Date of deposit | 31 May 2006 (31.05.2006) |
| 3-3-4 | Accession Number | CNCM I-3614 |
| 3-5 | Designated States for Which Indications are Made | all designations |
| 4 | The indications made below relate to the deposited microorganism(s) or other biological material referred to in the description on: | |
| 4-1 | page | p27, p53 |
| 4-2 | line | 114, 116 |
| 4-3 | Identification of deposit | |
| 4-3-1 | Name of depositary institution | CNCM Collection nationale de cultures de micro-organismes |
| 4-3-2 | Address of depositary institution | Institut Pasteur, 28, rue du Dr Roux, 75724 Paris Cedex 15, France |

-continued

| | | |
|---|---|---|
| 4-3-3 | Date of deposit | 31 May 2006 (31.05.2006) |
| 4-3-4 | Accession Number | CNCM I-3615 |
| 4-5 | Designated States for Which Indications are Made | all designations |
| 5 | The indications made below relate to the deposited microorganism(s) or other biological material referred to in the description on: | |
| 5-1 | page | p28, p54 |
| 5-2 | line | 117, 119 |
| 5-3 | Identification of deposit | |
| 5-3-1 | Name of depositary institution | CNCM Collection nationale de cultures de micro-organismes |
| 5-3-2 | Address of depositary institution | Institut Pasteur, 28, rue du Dr Roux, 75724 Paris Cedex 15, France |
| 5-3-3 | Date of deposit | 31 May 2006 (31.05.2006) |
| 5-3-4 | Accession Number | CNCM i-3616 |
| 5-5 | Designated States for Which Indications are Made | all designations |

| FOR RECEIVING OFFICE USE ONLY | | | FOR INTERNATIONAL BUREAU USE ONLY | | |
|---|---|---|---|---|---|
| 0-4 | This form was received with the international application: (yes or no) | | 0-5 | This form was received by the international Bureau on: | |
| 0-4-1 | Authorized officer | | 0-5-1 | Authorized officer | |

The invention claimed is:

1. A method for generating in vitro an antibody, or one of its functional fragments directed against a tumoral antigen expressed at the surface of a tumor resistant to at least one anti-tumoral compound, the method comprising:
   (a) immunizing second animals directly with a milled homogenate and/or a suspension and/or a cell lysate stemming from said resistant tumor, wherein the immunized second animals produce antibodies to the tumoral antigen expressed at the surface of the tumor resistant to the anti-tumoral compound, and
   (b) screening antibodies produced by the immunized second animals for antibodies and functional fragments thereof that specifically recognize the tumoral antigen expressed at the surface of the resistant tumor and not expressed at the surface of the native tumor from which the resistant tumor was derived;

wherein said resistant tumor is produced by grafting a tumor line and/or all or part of a human tumor on a first animal and then treating the first animal by administering the anti-tumoral compound for which it is desired to induce a resistance in the native tumor and said anti-tumoral compound comprises at least one monoclonal antibody.

2. The method according to claim 1, characterized in that said immunization is carried out via intraperitoneal and/or subcutaneous and/or intravenous and/or intrasplenic injection.

3. The method according to claim 1, characterized in that said antibody, or one of its functional fragments, directed against a tumoral antigen expressed at the surface of said resistant tumor is a monoclonal antibody.

4. The method according to claim 1, characterized in that said antibody, or one of its functional fragments is an immunoglobulin selected from the group consisting of an IgG, an IgA, an IgM, an IgD, and an IgE.

5. The method according to claim 4, characterized in that said antibody, or one of its functional fragments, is an IgG of gamma 1, gamma 2 or gamma 4 isotype.

6. The method according to claim 1, characterized in that said functional fragment is selected from Fv, Fab, (Fab')2, Fab', scFv, scFv-Fc fragments and diabodies.

7. The method according to claim 1, characterized in that it comprises the following steps:
  i) directly immunizing the second animal with the milled homogenate and/or the suspension and/or the cell lysate stemming from the resistant tumor,
  ii) fusing cells from the spleen of the immunized second animal of step i) with myeloma cells in order to obtain hybridomas, and
  iii) selecting by differential selection the hybridomas secreting antibodies which specifically recognize the antigens expressed at the surface of the tumoral cells of the resistant tumor and whose expression is induced by the anti-tumoral treatment.

8. The method according to claim 7, characterized in that it further comprises, prior to step i), the following steps:
  a) selecting and grafting on first animals a tumoral line and/or all or part of a native tumor,
  b) treating a portion of these grafted first animals with at least one anti-tumoral compound to produce a resistant tumor,
  c) recovering all or part of the native tumor from the untreated first animals grafted in step a),
  d) recovering all or part of the resistant tumor from the first animals treated in step b),
  e) preparing a means for differential selection of the antibodies from tumors entirely or partly recovered in steps c) and d) respectively, and
  f) preparing a milled homogenate and/or a cell lysate from resistant tumors entirely or partly recovered in step d).

9. The method according to claim 8, characterized in that said tumor line and/or native tumor is selected from the group consisting of lung tumors, colon tumors, prostate tumors, breast tumors, and ovary tumor cells for which resistances to treatments are ascertained.

10. The method according to claim 1, characterized in that said at least one anti-tumoral compound is selected from the group consisting of chemotherapy agents, radiotherapy agents, hormonotherapy agents, chemical molecules and antibodies.

11. The method according to claim 1, characterized in that said antibody is a monoclonal antibody or a functional fragment thereof that recognizes (a) growth factor receptors, (b) molecules involved in angiogenesis, or (c) chemokines or integrins involved in cell migration.

12. The method according to claim 1, characterized in that said at least one anti-tumoral compound comprises a combination of at least two anti-tumoral compounds of different nature, and/or having different action mechanisms, and/or targeting different proteins.

13. The method according to claim 12, characterized in that said combination of anti-tumoral compounds comprises a combination of monoclonal antibodies or of their functional fragments.

14. The method according to claim 13, characterized in that said combination of monoclonal antibodies comprises monoclonal antibodies selected from the group consisting of anti-IGF-IR, anti-EGFR, anti-Her/2neu, anti-VEGF, anti-VEGFR, anti-CXCR, anti-cMET, and anti-RON antibodies.

15. The method according to claim 14, characterized in that said combination consists of the combination of an anti-IGF-IR antibody, an anti-EGFR antibody and an anti-Her/2neu antibody.

16. The method according to claim 15, characterized in that said combination consists of anti-IGF-IR monoclonal antibody 7C10, anti-EGFR monoclonal antibody 225 and anti-Her/2neu receptor monoclonal antibody h4D5.

17. The method according to claim 1, characterized in that it comprises the following steps:
  i) directly immunizing the second animal with the milled homogenate and/or the suspension and/or the cell lysate stemming from the resistant tumor,
  ii) fusing cells from the spleen of the immunized second animal of step i) with myeloma cells in order to obtain hybridomas, and
  iii) selecting hybridomas secreting antibodies which do not recognize the antigens of the native tumoral cell by differential screening of the antibodies secreted by the hybridomas between the native tumor and the resistant tumor.

18. The method according to claim 17, characterized in that said differential screening comprises
  a) selecting and grafting on first animals a tumoral line and/or all or part of a native tumor,
  b) treating a portion of these grafted first animals with at least one anti-tumoral compound to produce a resistant tumor,
  c) recovering all or part of the native tumor from the untreated first animals grafted in step a),
  d) recovering all or part of the resistant tumor from the first animals treated in step b),
  e) preparing a means for differential selection of the antibodies from tumors entirely or partly recovered in steps c) and d) respectively.

19. The method according to claim 8, further comprising a tolerization step prior to step i).

20. The method according to claim 19, characterized in that said tolerization step consists of:
  administering to the second animals a milled homogenate and/or a suspension and/or a cell lysate obtained from native tumors from step c), and
  treating the second animals with native tumors with an immunosuppressor thereby removing the B cells activated by the administration of the preceding step and thereby inhibiting a response against said native tumor.

21. A method for generating and selecting in vitro an antibody, or one of its functional fragments, wherein the antibody or one of its function fragments is (a) capable of inhibiting the resistance of a tumor to an anti-tumoral compound or (b) specifically recognizes a tumoral antigen expressed at the surface of a tumor resistant to at least one anti-tumoral compound, said tumoral antigen being involved in the resistance of said tumor to the anti-tumoral compound, the method comprising:
  a) generating in vitro an antibody, or one of its functional fragments, according to the method of claim 1, said antibody being directed against said tumoral antigen specifically expressed at the surface of the resistant tumor, said tumoral antigen not being expressed at the surface of the cells of a native tumor from which the resistant tumor is derived;

b) contacting the antibody obtained in step a) either in vitro or in vivo with the tumor resistant to the anti-tumoral compound; and c) selecting said antibody if an inhibitory effect by this antibody is demonstrated on the resistance of the tumor to the anti-tumoral compound.

22. The method according to claim 1, wherein the antibody is a therapeutic and/or diagnostic monoclonal antibody.

23. A method for identifying novel therapeutic and/or diagnostic targets, either intracellular or extracellular, involved in resistance phenomena comprising:

generating an antibody according to the method of claim 1, wherein the antibody is a monoclonal antibody; and identifying a protein recognized by said monoclonal antibody.

* * * * *

SEQUENCE LISTING

```
<160> NUMBER OF SEQ ID NOS: 80

<210> SEQ ID NO 1
<211> LENGTH: 11
<212> TYPE: PRT
<213> ORGANISM: Mus musculus

<400> SEQUENCE: 1

Arg Ala Arg Gln Asp Ile Arg Asn Phe Leu Asn
1               5                   10

<210> SEQ ID NO 2
<211> LENGTH: 7
<212> TYPE: PRT
<213> ORGANISM: mus musculus

<400> SEQUENCE: 2

Tyr Thr Ser Arg Leu His Ser
1               5

<210> SEQ ID NO 3
<211> LENGTH: 9
<212> TYPE: PRT
<213> ORGANISM: mus musculus

<400> SEQUENCE: 3

Gln Gln Gly Asn Thr Leu Pro Phe Thr
1               5

<210> SEQ ID NO 4
<211> LENGTH: 6
<212> TYPE: PRT
<213> ORGANISM: mus musculus

<400> SEQUENCE: 4
```

```
Thr Glu Tyr Thr Leu His
  1               5

<210> SEQ ID NO 5
<211> LENGTH: 17
<212> TYPE: PRT
<213> ORGANISM: mus musculus

<400> SEQUENCE: 5

Gly Ile Asp Pro Asn Asn Gly Gly Thr Ser Tyr Asn Gln Lys Phe Lys
  1               5                  10                  15

Gly

<210> SEQ ID NO 6
<211> LENGTH: 8
<212> TYPE: PRT
<213> ORGANISM: mus musculus

<400> SEQUENCE: 6

Ser Asn Ser Tyr Tyr Phe Asp Tyr
  1               5

<210> SEQ ID NO 7
<211> LENGTH: 117
<212> TYPE: PRT
<213> ORGANISM: mus musculus

<400> SEQUENCE: 7

Glu Val Gln Leu Gln Gln Ser Gly Pro Glu Leu Val Lys Pro Gly Ala
  1               5                  10                  15

Ser Val Lys Ile Ser Cys Lys Thr Ser Gly Tyr Thr Phe Thr Glu Tyr
                 20                  25                  30

Thr Leu His Trp Val Lys Gln Ser His Gly Lys Ser Leu Glu Trp Ile
             35                  40                  45

Gly Gly Ile Asp Pro Asn Asn Gly Gly Thr Ser Tyr Asn Gln Lys Phe
         50                  55                  60

Lys Gly Lys Ala Thr Leu Thr Val Asp Lys Ser Ser Thr Ala Tyr
 65                  70                  75                  80

Met Glu Leu Arg Ser Leu Thr Ser Glu Asp Ser Ala Val Tyr Leu Cys
                 85                  90                  95

Ala Arg Ser Asn Ser Tyr Tyr Phe Asp Tyr Trp Gly Gln Gly Thr Thr
                100                 105                 110

Leu Thr Val Ser Ser
            115

<210> SEQ ID NO 8
<211> LENGTH: 107
<212> TYPE: PRT
<213> ORGANISM: mus musculus

<400> SEQUENCE: 8

Asp Ile Gln Met Thr Gln Thr Thr Ser Ser Leu Ser Ala Ser Leu Gly
  1               5                  10                  15

Asp Ser Val Thr Ile Ser Cys Arg Ala Arg Gln Asp Ile Arg Asn Phe
                 20                  25                  30

Leu Asn Trp Tyr Gln Gln Arg Pro Asp Gly Thr Val Lys Leu Leu Ile
             35                  40                  45

Tyr Tyr Thr Ser Arg Leu His Ser Gly Val Pro Ser Arg Phe Ser Gly
         50                  55                  60
```

```
Ser Gly Ser Gly Thr Asp Tyr Ser Leu Thr Ile Ser Asn Leu Asp Gln
65                  70                  75                  80

Glu Asp Val Ala Thr Tyr Phe Cys Gln Gln Gly Asn Thr Leu Pro Phe
                85                  90                  95

Thr Phe Gly Ser Gly Thr Lys Leu Glu Ile Lys
            100                 105

<210> SEQ ID NO 9
<211> LENGTH: 11
<212> TYPE: PRT
<213> ORGANISM: mus musculus

<400> SEQUENCE: 9

Arg Ala Ser Gly Asn Ile His Asn Tyr Leu Ala
1               5                   10

<210> SEQ ID NO 10
<211> LENGTH: 7
<212> TYPE: PRT
<213> ORGANISM: mus musculus

<400> SEQUENCE: 10

Asn Ala Lys Thr Leu Ala Asp
1               5

<210> SEQ ID NO 11
<211> LENGTH: 9
<212> TYPE: PRT
<213> ORGANISM: mus musculus

<400> SEQUENCE: 11

Gln His Phe Trp Thr Thr Pro Tyr Thr
1               5

<210> SEQ ID NO 12
<211> LENGTH: 6
<212> TYPE: PRT
<213> ORGANISM: mus musclus

<400> SEQUENCE: 12

Thr Asn Tyr Gly Met Asn
1               5

<210> SEQ ID NO 13
<211> LENGTH: 16
<212> TYPE: PRT
<213> ORGANISM: mus musculus

<400> SEQUENCE: 13

Trp Ile Asn Thr Tyr Thr Gly Glu Pro Thr Tyr Ala Asp Asp Phe Lys
1               5                   10                  15

<210> SEQ ID NO 14
<211> LENGTH: 9
<212> TYPE: PRT
<213> ORGANISM: mus musculus

<400> SEQUENCE: 14

Gly Gly Tyr Tyr Arg Tyr Ala Ala Tyr
1               5

<210> SEQ ID NO 15
<211> LENGTH: 118
<212> TYPE: PRT
<213> ORGANISM: mus musculus
```

<400> SEQUENCE: 15

Gln Ile Gln Leu Val Gln Ser Gly Pro Glu Leu Lys Lys Pro Gly Glu
1               5                   10                  15

Thr Val Lys Ile Ser Cys Lys Ala Ser Gly Gln Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Gly Tyr Tyr Arg Tyr Ala Ala Tyr Trp Gly Gln Gly Thr
            100                 105                 110

Leu Val Thr Val Ser Ala
            115

<210> SEQ ID NO 16
<211> LENGTH: 107
<212> TYPE: PRT
<213> ORGANISM: mus musculus

<400> SEQUENCE: 16

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Cys Tyr Phe Cys Gln His Phe Trp Thr Thr Pro Tyr
                85                  90                  95

Thr Phe Gly Gly Gly Thr Lys Leu Glu Leu Ile
            100                 105

<210> SEQ ID NO 17
<211> LENGTH: 17
<212> TYPE: PRT
<213> ORGANISM: mus musculus

<400> SEQUENCE: 17

Lys Ala Ser Gln Ser Leu Leu Asn Ser Arg Thr Arg Lys Asn Tyr Leu
1               5                   10                  15

Ala

<210> SEQ ID NO 18
<211> LENGTH: 7
<212> TYPE: PRT
<213> ORGANISM: mus musculus

<400> SEQUENCE: 18

Trp Ala Ser Thr Arg Glu Ser
1               5

```
<210> SEQ ID NO 19
<211> LENGTH: 8
<212> TYPE: PRT
<213> ORGANISM: mus musculus

<400> SEQUENCE: 19

Lys Gln Ser Tyr Asn Leu Tyr Thr
1               5

<210> SEQ ID NO 20
<211> LENGTH: 5
<212> TYPE: PRT
<213> ORGANISM: mus musculus

<400> SEQUENCE: 20

Asp Thr Tyr Met His
1               5

<210> SEQ ID NO 21
<211> LENGTH: 17
<212> TYPE: PRT
<213> ORGANISM: mus musculus

<400> SEQUENCE: 21

Arg Ile Asp Pro Ala Asn Gly Asn Thr Lys Ser Asp Pro Lys Phe Gln
1               5                   10                  15

Gly

<210> SEQ ID NO 22
<211> LENGTH: 10
<212> TYPE: PRT
<213> ORGANISM: mus musculus

<400> SEQUENCE: 22

Gly Tyr Thr Asn Tyr Val Trp Phe Thr Tyr
1               5                   10

<210> SEQ ID NO 23
<211> LENGTH: 119
<212> TYPE: PRT
<213> ORGANISM: mus musculus

<400> SEQUENCE: 23

Glu Val Gln Leu Gln Gln Ser Gly Ala Glu Val Val Lys Pro Gly Ala
1               5                   10                  15

Ser Val Lys Leu Ser Cys Thr Ala Ser Gly Phe Asn Ile Lys Asp Thr
                20                  25                  30

Tyr Met His Trp Val Lys Gln Arg Pro Glu Gln Gly Leu Glu Trp Ile
            35                  40                  45

Gly Arg Ile Asp Pro Ala Asn Gly Asn Thr Lys Ser Asp Pro Lys Phe
        50                  55                  60

Gln Gly Lys Ala Ile Lys Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Ser Gly Tyr Thr Asn Tyr Val Trp Phe Thr Tyr Trp Gly Gln Gly
            100                 105                 110

Thr Leu Val Thr Val Ser Ala
        115

<210> SEQ ID NO 24
```

<211> LENGTH: 112
<212> TYPE: PRT
<213> ORGANISM: mus musculus

<400> SEQUENCE: 24

Asp Ile Val Met Ser Gln Ser Pro Ser Ser Leu Ala Val Ala Ala Gly
1               5                   10                  15

Glu Lys Val Thr Met Ser Cys Lys Ala Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Ser Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Tyr Thr Phe Gly Gly Gly Thr Lys Leu Glu Ile Lys
            100                 105                 110

<210> SEQ ID NO 25
<211> LENGTH: 11
<212> TYPE: PRT
<213> ORGANISM: mus musculus

<400> SEQUENCE: 25

Lys Ala Ser Gln Asp Val Ser Thr Ala Val Ala
1               5                   10

<210> SEQ ID NO 26
<211> LENGTH: 7
<212> TYPE: PRT
<213> ORGANISM: mus musculus

<400> SEQUENCE: 26

Ser Ala Ser Tyr Arg Tyr Thr
1               5

<210> SEQ ID NO 27
<211> LENGTH: 9
<212> TYPE: PRT
<213> ORGANISM: mus musculus

<400> SEQUENCE: 27

Gln Gln His Tyr Ser Asn Pro Arg Thr
1               5

<210> SEQ ID NO 28
<211> LENGTH: 6
<212> TYPE: PRT
<213> ORGANISM: mus musculus

<400> SEQUENCE: 28

Ser Ser Tyr Gly Val His
1               5

<210> SEQ ID NO 29
<211> LENGTH: 16
<212> TYPE: PRT
<213> ORGANISM: mus musculus

<400> SEQUENCE: 29

Val Ile Trp Val Gly Gly Thr Thr Asn Phe Lys Ser Ala Leu Met Ser

```
1               5                   10                  15
```

<210> SEQ ID NO 30
<211> LENGTH: 10
<212> TYPE: PRT
<213> ORGANISM: mus musculus

<400> SEQUENCE: 30

```
Glu Arg Pro Tyr Gly Asn Pro Leu Val Asp
1               5                   10
```

<210> SEQ ID NO 31
<211> LENGTH: 118
<212> TYPE: PRT
<213> ORGANISM: mus musculus

<400> SEQUENCE: 31

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Ser Tyr
            20                  25                  30

Gly Val His Trp Val Arg Gln Pro Pro Gly Lys Gly Leu Glu Trp Leu
        35                  40                  45

Gly Val Ile Trp Val Gly Gly Thr Thr Asn Phe Lys Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Glu Arg Pro Tyr Gly Asn Pro Leu Val Asp Trp Gly Gln Gly Thr
            100                 105                 110

Leu Val Thr Val Ser Ala
        115
```

<210> SEQ ID NO 32
<211> LENGTH: 107
<212> TYPE: PRT
<213> ORGANISM: mus musculus

<400> SEQUENCE: 32

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Asn Pro Arg
                85                  90                  95

Thr Phe Gly Gly Gly Thr Lys Leu Glu Ile Lys
            100                 105
```

<210> SEQ ID NO 33
<211> LENGTH: 16
<212> TYPE: PRT
<213> ORGANISM: mus musculus

```
<400> SEQUENCE: 33

Arg Ser Ser Gln Thr Ile Val His Ser Asn Gly Asn Thr Tyr Leu Glu
1               5                   10                  15

<210> SEQ ID NO 34
<211> LENGTH: 7
<212> TYPE: PRT
<213> ORGANISM: mus musculus

<400> SEQUENCE: 34

Lys Val Ser Asn Arg Phe Ser
1               5

<210> SEQ ID NO 35
<211> LENGTH: 9
<212> TYPE: PRT
<213> ORGANISM: mus musculus

<400> SEQUENCE: 35

Phe Gln Ser Ser Arg Val Pro Tyr Thr
1               5

<210> SEQ ID NO 36
<211> LENGTH: 6
<212> TYPE: PRT
<213> ORGANISM: mus musculus

<400> SEQUENCE: 36

Thr Asn Tyr Trp Leu Gly
1               5

<210> SEQ ID NO 37
<211> LENGTH: 17
<212> TYPE: PRT
<213> ORGANISM: mus musculus

<400> SEQUENCE: 37

Asp Ile Phe Pro Gly Gly Ile Tyr Thr Asn Tyr Asn Glu Lys Ile Lys
1               5                   10                  15

Gly

<210> SEQ ID NO 38
<211> LENGTH: 10
<212> TYPE: PRT
<213> ORGANISM: mus musculus

<400> SEQUENCE: 38

Phe Asp Asp Phe Asp Pro Phe Phe Ala Ser
1               5                   10

<210> SEQ ID NO 39
<211> LENGTH: 119
<212> TYPE: PRT
<213> ORGANISM: mus musculus

<400> SEQUENCE: 39

Gln Val Gln Leu Gln Gln Ser Gly Pro Glu Leu Val Arg Pro Gly Thr
1               5                   10                  15

Ser Val Lys Ile Ser Cys Lys Ala Ser Gly Tyr Thr Phe Thr Asn Tyr
                20                  25                  30

Trp Leu Gly Trp Val Lys Gln Arg Pro Gly His Gly Leu Glu Trp Ile
            35                  40                  45

Gly Asp Ile Phe Pro Gly Gly Ile Tyr Thr Asn Tyr Asn Glu Lys Ile
```

```
                50                  55                  60
Lys Gly Glu Ala Thr Leu Thr Ala Asp Thr Ser Ser Thr Ala Tyr
 65                  70                  75                  80

Leu Gln Leu Ser Ser Leu Thr Ser Glu Asp Ser Phe Val Tyr Phe Cys
                 85                  90                  95

Ala Arg Phe Asp Asp Phe Asp Pro Phe Phe Ala Ser Trp Gly Gln Gly
            100                 105                 110

Thr Leu Val Thr Val Ser Ala
            115

<210> SEQ ID NO 40
<211> LENGTH: 112
<212> TYPE: PRT
<213> ORGANISM: mus musculus

<400> SEQUENCE: 40

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Thr Ile Val His Ser
             20                  25                  30

Asn Gly Asn Thr Tyr Leu Glu Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Asn Ile
 65                  70                  75                  80

Ser Arg Val Glu Ala Glu Asp Leu Gly Ile Tyr Tyr Cys Phe Gln Ser
                 85                  90                  95

Ser Arg Val Pro Tyr Thr Phe Gly Gly Gly Thr Lys Leu Glu Ile Lys
            100                 105                 110

<210> SEQ ID NO 41
<211> LENGTH: 33
<212> TYPE: DNA
<213> ORGANISM: mus musculus

<400> SEQUENCE: 41
agggcaaggc aggacattcg caatttttta aac                            33

<210> SEQ ID NO 42
<211> LENGTH: 21
<212> TYPE: DNA
<213> ORGANISM: mus musculus

<400> SEQUENCE: 42
tacacctcaa gattacactc a                                         21

<210> SEQ ID NO 43
<211> LENGTH: 27
<212> TYPE: DNA
<213> ORGANISM: mus musculus

<400> SEQUENCE: 43
caacagggta atacgcttcc attcacg                                   27

<210> SEQ ID NO 44
<211> LENGTH: 18
<212> TYPE: DNA
<213> ORGANISM: mus musculus

<400> SEQUENCE: 44
```

```
actgaataca ccttgcac                                                  18

<210> SEQ ID NO 45
<211> LENGTH: 51
<212> TYPE: DNA
<213> ORGANISM: mus musculus

<400> SEQUENCE: 45
ggtattgatc ctaacaatgg tggtactagc tataaccaga agttcaaggg c              51

<210> SEQ ID NO 46
<211> LENGTH: 24
<212> TYPE: DNA
<213> ORGANISM: mus musculus

<400> SEQUENCE: 46
tcgaacagtt actactttga ctac                                           24

<210> SEQ ID NO 47
<211> LENGTH: 351
<212> TYPE: DNA
<213> ORGANISM: mus musculus

<400> SEQUENCE: 47
gaggtccagc tgcaacagtc tggacctgag ctggtgaagc ctggggcttc agtgaagata    60
tcctgcaaga cttctggata cacattcact gaatacacct tgcactgggt gaagcagagc   120
catggaaaga gccttgagtg gattggaggt attgatccta acaatggtgg tactagctat   180
aaccagaagt tcaagggcaa ggccacattg actgtagaca gtcctccag cacagcctac    240 atggagctcc gcagcctgac atctgaggat tctgcagtct atctctgtgc aagatcgaac   300
agttactact ttgactactg gggccaaggc accactctca cagtctcctc a            351

<210> SEQ ID NO 48
<211> LENGTH: 321
<212> TYPE: DNA
<213> ORGANISM: mus musculus

<400> SEQUENCE: 48
gatatccaga tgacacagac tacatcctcc ctgtctgcct ctctgggaga cagcgtcacc    60
atcagttgca gggcaaggca ggacattcgc aattttttaa actggtatca gcagagacca   120
gatggaactg ttaaactcct gatctactac acctcaagat acactcagg agtcccatca    180 aggttcagtg gcagtgggtc tggaacagat tattctctca ccattagcaa cctggaccaa   240
gaagatgttg ccacttattt ttgccaacag ggtaatacgc ttccattcac gttcggctcg   300
gggacaaagt tggaaataaa a                                             321

<210> SEQ ID NO 49
<211> LENGTH: 33
<212> TYPE: DNA
<213> ORGANISM: mus musculus

<400> SEQUENCE: 49
cgagcaagtg ggaatattca caattattta gca                                 33

<210> SEQ ID NO 50
<211> LENGTH: 21
<212> TYPE: DNA
<213> ORGANISM: mus musculus

<400> SEQUENCE: 50
```
aatgcaaaaa ccttagcaga t                                             21

<210> SEQ ID NO 51
<211> LENGTH: 27
<212> TYPE: DNA
<213> ORGANISM: mus musculus

<400> SEQUENCE: 51 caacatttttt ggactactcc gtacaca                                      27

<210> SEQ ID NO 52
<211> LENGTH: 18
<212> TYPE: DNA
<213> ORGANISM: mus musculus

<400> SEQUENCE: 52
acaaactatg gaatgaac                                                 18

<210> SEQ ID NO 53
<211> LENGTH: 48
<212> TYPE: DNA
<213> ORGANISM: mus musculus

<400> SEQUENCE: 53
tggataaaca cctacactgg agagccaaca tatgctgatg acttcaag                48

<210> SEQ ID NO 54
<211> LENGTH: 27
<212> TYPE: DNA
<213> ORGANISM: mus musculus

<400> SEQUENCE: 54
gggggctact ataggtacgc ggcttac                                       27

<210> SEQ ID NO 55
<211> LENGTH: 354
<212> TYPE: DNA
<213> ORGANISM: mus musculus

<400> SEQUENCE: 55
cagatccagt tggtgcagtc tggacctgag ctgaagaagc ctggagagac agtcaagatc    60
tcctgcaagg cttctgggca gaccttcaca aactatggaa tgaactgggt gaagcaggct   120
ccaggaaagg gtttaaagtg gatgggctgg ataaacacct acactggaga gccaacatat   180
gctgatgact tcaagggacg gtttgccttc tctttggaaa cctctgccag cactgcctat   240
ttgcagatca caaccctcaa aaatgaggac acggctacat atttctgtgc aagagggggc   300
tactataggt acgcggctta ctggggccaa gggactctgg tcactgtctc tgca         354

<210> SEQ ID NO 56
<211> LENGTH: 321
<212> TYPE: DNA
<213> ORGANISM: mus musculus

<400> SEQUENCE: 56
gacatccaga tgactcagtc tccagcctcc ctatctgcat ctgtgggaga aactgtcacc    60
atcacatgtc gagcaagtgg gaatattcac aattatttag catggtatca gcagaaacag   120
ggaaaatctc ctcagctcct ggtctataat gcaaaaacct tagcagatgg tgtgccatca   180
aggttcagtg gcagtggatc aggaacacaa tattctctca agatcaacag cctgcagcct   240
gaagattttg ggtgttattt ctgtcaacat ttttggacta ctccgtacac attcggaggg   300

```
gggaccaaac tggaactaat a                                              321

<210> SEQ ID NO 57
<211> LENGTH: 51
<212> TYPE: DNA
<213> ORGANISM: mus musculus

<400> SEQUENCE: 57
aaagccagtc agagtctgct caacagtaga acccgaaaga actacttggc t              51

<210> SEQ ID NO 58
<211> LENGTH: 21
<212> TYPE: DNA
<213> ORGANISM: mus musculus

<400> SEQUENCE: 58
tgggcatcca ctagggaatc t                                               21

<210> SEQ ID NO 59
<211> LENGTH: 24
<212> TYPE: DNA
<213> ORGANISM: mus musculus

<400> SEQUENCE: 59
aagcaatctt ataatctgta cacg                                            24

<210> SEQ ID NO 60
<211> LENGTH: 15
<212> TYPE: DNA
<213> ORGANISM: mus musculus

<400> SEQUENCE: 60
gacacctata tgcac                                                      15

<210> SEQ ID NO 61
<211> LENGTH: 51
<212> TYPE: DNA
<213> ORGANISM: mus musculus

<400> SEQUENCE: 61
aggattgatc ctgcgaatgg aaatactaaa tctgacccga agttccaggg c              51

<210> SEQ ID NO 62
<211> LENGTH: 30
<212> TYPE: DNA
<213> ORGANISM: mus musculus

<400> SEQUENCE: 62
ggatatacta actacgtttg gtttacttac                                      30

<210> SEQ ID NO 63
<211> LENGTH: 357
<212> TYPE: DNA
<213> ORGANISM: mus musculus

<400> SEQUENCE: 63
gaggttcagc tgcagcagtc tggggcagag gttgtgaagc caggggcctc agtcaagttg     60
tcctgcacag cttctggctt caacattaaa gacacctata tgcactgggt gaaacagagg    120
cctgaacagg gcctggagtg gattggaagg attgatcctg cgaatggaaa tactaaatct    180
gacccgaagt tccagggcaa ggccattaaa acagcagaca catcctccaa cacagcctac    240
cttcagctca gtagcctgac atctgaggac actgccgtct attactgtac tagcggatat    300
```

```
actaactacg tttggtttac ttactggggc aagggactc tggtcactgt ctctgca      357

<210> SEQ ID NO 64
<211> LENGTH: 336
<212> TYPE: DNA
<213> ORGANISM: mus musculus

<400> SEQUENCE: 64
gacattgtga tgtcacagtc tccatcctcc ctggctgtgg cagcaggaga gaaggtcact      60
atgagctgca aagccagtca gagtctgctc aacagtagaa cccgaaagaa ctacttggct     120
tggtaccagc agaaaccagg gcagtctcct aaactgctga tctactgggc atccactagg     180
gaatctgggg tccctgatcg cttcacaggc agtggatctg ggacagattt cagtctcacc     240
atcagcagtg tgcaggctga agacctggca gtttattact gcaagcaatc ttataatctg     300
tacacgttcg gagggggac caagctggaa ataaaa                                336

<210> SEQ ID NO 65
<211> LENGTH: 33
<212> TYPE: DNA
<213> ORGANISM: mus musculus

<400> SEQUENCE: 65
aaggccagtc aggatgtgag tactgctgtc gcc                                   33

<210> SEQ ID NO 66
<211> LENGTH: 21
<212> TYPE: DNA
<213> ORGANISM: mus musculus

<400> SEQUENCE: 66
tcggcatcct accgttacac t                                                21

<210> SEQ ID NO 67
<211> LENGTH: 30
<212> TYPE: DNA
<213> ORGANISM: mus musculus

<400> SEQUENCE: 67
cagcaacatt atagtaatcc tcggacgttc                                       30

<210> SEQ ID NO 68
<211> LENGTH: 18
<212> TYPE: DNA
<213> ORGANISM: mus musculus

<400> SEQUENCE: 68
tccagctatg gtgtacac                                                    18

<210> SEQ ID NO 69
<211> LENGTH: 48
<212> TYPE: DNA
<213> ORGANISM: mus musculus

<400> SEQUENCE: 69
gtaatatggg ttggtggaac cacaaatttt aaatcggctc tcatgtcc                   48

<210> SEQ ID NO 70
<211> LENGTH: 30
<212> TYPE: DNA
<213> ORGANISM: mus musculus

<400> SEQUENCE: 70
```

```
gagagaccct atggtaaccc tttggttgac                                      30
```

<210> SEQ ID NO 71
<211> LENGTH: 354
<212> TYPE: DNA
<213> ORGANISM: mus musculus

<400> SEQUENCE: 71

```
caggtgcagc tgaaggagtc aggacctggc ctggtggcgc cctcacagag cctgtccatc     60
acttgcactg tctctgggtt ttcattatcc agctatggtg tacactgggt tcgccagcct    120
ccaggaaagg gtctggagtg gctgggagta atatggggttg gtggaaccac aaattttaaa   180
tcggctctca tgtccagact gagcatcagc aaagacaact ccaagagcca agttttctta    240
aaaatgaaca gtctgcaaac tgatgacaca gccatgtact actgtgccag agagaccc      300
tatggtaacc ctttggttga ctggggccaa gggactctgg tcactgtctc tgca           354
```

<210> SEQ ID NO 72
<211> LENGTH: 321
<212> TYPE: DNA
<213> ORGANISM: mus musculus

<400> SEQUENCE: 72

```
gacattgtga tgacccagtc tcacaaattc atgtccacat cagtaggaga cagggtcagc     60
atcacctgca aggccagtca ggatgtgagt actgctgtcg cctggtatca acagaaacca    120
ggacaatctc ctaaactact gatttactcg gcatcctacc gttacactgg agtccctgat    180
cgcttcactg gcagtggatc tgggacggat ttcactttca ccatcagcag tgtgcaggct    240
gaagacctgg cagtttatta ctgtcagcaa cattatagta atcctcggac gttcggtgga    300
ggcaccaagc tggaaatcaa a                                              321
```

<210> SEQ ID NO 73
<211> LENGTH: 48
<212> TYPE: DNA
<213> ORGANISM: mus musculus

<400> SEQUENCE: 73

```
agatctagtc agaccattgt acatagtaat ggaaacacct atttagaa                  48
```

<210> SEQ ID NO 74
<211> LENGTH: 21
<212> TYPE: DNA
<213> ORGANISM: mus musculus

<400> SEQUENCE: 74

```
aaagtttcca accgattttc t                                               21
```

<210> SEQ ID NO 75
<211> LENGTH: 27
<212> TYPE: DNA
<213> ORGANISM: mus musculus

<400> SEQUENCE: 75

```
tttcaaagtt cacgtgttcc gtacacg                                         27
```

<210> SEQ ID NO 76
<211> LENGTH: 27
<212> TYPE: DNA
<213> ORGANISM: mus musculus

<400> SEQUENCE: 76

-continued

```
<210> SEQ ID NO 77
<211> LENGTH: 51
<212> TYPE: DNA
<213> ORGANISM: mus musculus

<400> SEQUENCE: 77
gatattttcc ctggaggtat ttatactaac tacaatgaga agatcaaggg c          51

<210> SEQ ID NO 78
<211> LENGTH: 30
<212> TYPE: DNA
<213> ORGANISM: mus musculus

<400> SEQUENCE: 78
tttgatgatt tcgaccccctt ttttgcttcc                                  30

<210> SEQ ID NO 79
<211> LENGTH: 357
<212> TYPE: DNA
<213> ORGANISM: mus musculus

<400> SEQUENCE: 79
caggtccagt tgcagcagtc tggacccgag ctggtaaggc ctgggacttc agtgaagata    60
tcctgcaagg cctctggcta caccttcact aactactggc taggttgggt aaagcagagg   120
cctggacatg gacttgagtg gattggagat attttccctg gaggtattta tactaactac   180
aatgagaaga tcaagggcga ggccacactg actgccgaca catcctccag cactgcctac   240
ttgcagctca gtagcctgac atctgaggac tcttttgtct atttctgtgc aaggtttgat   300
gatttcgacc cctttttttgc ttcctgggggc caagggactc tggtcactgt ctctgca     357

<210> SEQ ID NO 80
<211> LENGTH: 336
<212> TYPE: DNA
<213> ORGANISM: mus musculus

<400> SEQUENCE: 80
gatgttttga tgacccaaac tccactctcc ctgcctgtca gtcttggaga tcaagcctcc    60
atctcttgca gatctagtca gaccattgta catagtaatg gaaacaccta tttagaatgg   120
tacctgcaga aaccaggcca gtctccaaag ctcctgatct acaaagtttc caaccgattt   180
tctggggtcc cagacaggtt cagtggcagt ggatcaggga cagatttcac actcaatatc   240
agcagagtgg aggctgagga tctgggaatt tattactgct ttcaaagttc acgtgttccg   300
tacacgttcg gaggggggac caagctggaa ataaaa                              336
```